United States Patent
Brockway et al.

(10) Patent No.: US 11,607,176 B2
(45) Date of Patent: Mar. 21, 2023

(54) SYSTEMS AND METHODS FOR DENOISING PHYSIOLOGICAL SIGNALS DURING ELECTRICAL NEUROMODULATION

(71) Applicant: Cardionomic, Inc., New Brighton, MN (US)

(72) Inventors: Marina Brockway, St. Paul, MN (US); Brian Brockway, St. Paul, MN (US); David Christopher Olson, New Brighton, MN (US); Steven D. Goedeke, New Brighton, MN (US); Michael C. Garrett, Northbrook, IL (US)

(73) Assignee: CARDIONOMIC, INC., New Brighton, MN (US)

( * ) Notice: Subject to any disclaimer, the term of this patent is extended or adjusted under 35 U.S.C. 154(b) by 0 days.

(21) Appl. No.: 17/520,131

(22) Filed: Nov. 5, 2021

(65) Prior Publication Data
US 2022/0054090 A1  Feb. 24, 2022

Related U.S. Application Data

(63) Continuation of application No. PCT/US2020/031358, filed on May 4, 2020.
(Continued)

(51) Int. Cl.
*A61B 5/316* (2021.01)
*A61B 5/00* (2006.01)
(Continued)

(52) U.S. Cl.
CPC .............. *A61B 5/7217* (2013.01); *A61B 5/28* (2021.01); *A61B 5/339* (2021.01); *A61B 5/725* (2013.01); *A61B 2562/046* (2013.01)

(58) Field of Classification Search
CPC ...... A61B 5/3616; A61B 5/7217; A61B 5/725
See application file for complete search history.

(56) References Cited

U.S. PATENT DOCUMENTS

| 4,718,423 A | 1/1988 | Willis et al. |
| 4,947,866 A | 8/1990 | Lessar et al. |

(Continued)

FOREIGN PATENT DOCUMENTS

| CA | 2 848 781 | 3/2013 |
| CN | 101797181 | 8/2010 |

(Continued)

OTHER PUBLICATIONS

Ardell et al., "Differential sympathetic regulation of automatic, conductile, and contractile tissue in dog heart," American Journal of Physiology (Nov. 1988) 255 (5): H1050-H1059.
(Continued)

*Primary Examiner* — Michael J D'Abreu
(74) *Attorney, Agent, or Firm* — Knobbe Martens Olson & Bear LLP

(57) ABSTRACT

Systems and methods are described for denoising, or filtering out, unwanted noise or interference, from biological or physiological parameter signals or waveforms such as ECG signals caused by application of electromagnetic energy (e.g., electrical stimulation) in a vicinity of sensors configured to obtain the biological or physiological parameter signals.

20 Claims, 16 Drawing Sheets

Related U.S. Application Data

(60) Provisional application No. 62/843,772, filed on May 6, 2019.

(51) Int. Cl.
*A61B 5/339* (2021.01)
*A61B 5/28* (2021.01)

(56) References Cited

U.S. PATENT DOCUMENTS

| | | |
|---|---|---|
| 4,950,227 A | 8/1990 | Savin et al. |
| 5,067,957 A | 11/1991 | Jervis |
| 5,156,154 A | 10/1992 | Vaienta, Jr. et al. |
| 5,190,546 A | 3/1993 | Jervis |
| 5,197,978 A | 3/1993 | Hess |
| 5,213,098 A | 5/1993 | Bennett et al. |
| 5,224,491 A | 7/1993 | Mehra |
| 5,259,387 A | 11/1993 | Depinto |
| 5,336,244 A | 8/1994 | Weijand |
| 5,345,936 A | 9/1994 | Pomeranz et al. |
| 5,365,926 A | 11/1994 | Desai |
| 5,383,852 A | 1/1995 | Stevens-Wright et al. |
| 5,423,881 A | 6/1995 | Breyen et al. |
| 5,431,649 A | 7/1995 | Mulier et al. |
| 5,462,527 A | 10/1995 | Stevens-Wright et al. |
| 5,465,717 A | 11/1995 | Imran et al. |
| 5,554,139 A | 9/1996 | Okajima |
| 5,564,434 A | 10/1996 | Halperin et al. |
| 5,598,848 A | 2/1997 | Swanson et al. |
| 5,611,777 A | 3/1997 | Bowden et al. |
| 5,711,316 A | 1/1998 | Elsberry et al. |
| 5,725,570 A | 3/1998 | Heath |
| 5,755,766 A | 5/1998 | Chastain et al. |
| 5,782,239 A | 7/1998 | Webster |
| 5,853,411 A | 12/1998 | Whayne et al. |
| 5,925,038 A | 7/1999 | Panescu et al. |
| 5,948,007 A | 9/1999 | Starkebaum et al. |
| 5,954,761 A | 9/1999 | Machek et al. |
| 5,968,040 A | 10/1999 | Swanson et al. |
| 5,997,563 A | 12/1999 | Kretzers |
| 6,036,697 A | 3/2000 | Dicaprio |
| 6,038,480 A | 3/2000 | Hrdlicka et al. |
| 6,058,331 A | 5/2000 | King et al. |
| 6,059,810 A | 5/2000 | Brown et al. |
| 6,071,308 A | 6/2000 | Ballou et al. |
| 6,099,526 A | 8/2000 | Whayne et al. |
| 6,123,723 A | 9/2000 | Konya et al. |
| 6,136,021 A | 10/2000 | Tockman et al. |
| 6,152,882 A | 11/2000 | Prutchi |
| 6,161,029 A | 12/2000 | Spreigl et al. |
| 6,223,072 B1 | 4/2001 | Mika et al. |
| 6,231,516 B1 | 5/2001 | Keilman et al. |
| 6,233,484 B1 | 5/2001 | Ben-haim et al. |
| 6,233,487 B1 | 5/2001 | Mika et al. |
| 6,236,887 B1 | 5/2001 | Ben-haim et al. |
| 6,241,724 B1 | 6/2001 | Fleischman et al. |
| 6,254,610 B1 | 7/2001 | Darvish et al. |
| 6,263,242 B1 | 7/2001 | Mika et al. |
| 6,266,564 B1 | 7/2001 | Hill et al. |
| 6,285,906 B1 | 9/2001 | Ben-haim et al. |
| 6,292,693 B1 | 9/2001 | Darvish et al. |
| 6,292,695 B1 | 9/2001 | Webster et al. |
| 6,292,704 B1 | 9/2001 | Malonek et al. |
| 6,295,475 B1 | 9/2001 | Morgan |
| 6,298,268 B1 | 10/2001 | Ben-haim et al. |
| 6,304,777 B1 | 10/2001 | Ben-haim et al. |
| 6,317,631 B1 | 11/2001 | Ben-haim et al. |
| 6,319,241 B1 | 11/2001 | King et al. |
| 6,330,476 B1 | 12/2001 | Ben-haim et al. |
| 6,335,538 B1 | 1/2002 | Prutchi et al. |
| 6,348,045 B1 | 2/2002 | Malonek et al. |
| 6,353,762 B1 | 3/2002 | Baudino et al. |
| 6,360,123 B1 | 3/2002 | Kimchi et al. |
| 6,360,126 B1 | 3/2002 | Mika et al. |
| 6,363,279 B1 | 3/2002 | Ben-haim et al. |
| 6,370,430 B1 | 4/2002 | Mika et al. |
| 6,409,750 B1 | 6/2002 | Hyodoh et al. |
| 6,415,178 B1 | 7/2002 | Ben-haim et al. |
| 6,424,866 B2 | 7/2002 | Mika et al. |
| 6,428,537 B1 | 8/2002 | Swanson et al. |
| 6,442,424 B1 | 8/2002 | Ben-haim et al. |
| 6,447,478 B1 | 9/2002 | Maynard |
| 6,459,928 B2 | 10/2002 | Mika et al. |
| 6,463,324 B1 | 10/2002 | Ben-haim et al. |
| 6,473,653 B1 | 10/2002 | Schallhorn et al. |
| 6,480,737 B1 | 11/2002 | Policker et al. |
| 6,522,904 B1 | 2/2003 | Mika et al. |
| 6,522,926 B1 | 2/2003 | Kieval et al. |
| 6,529,778 B2 | 3/2003 | Prutchi |
| 6,542,774 B2 | 4/2003 | Hill et al. |
| 6,547,788 B1 | 4/2003 | Maguire et al. |
| 6,564,096 B2 | 5/2003 | Mest |
| 6,571,127 B1 | 5/2003 | Ben-haim et al. |
| 6,574,492 B1 | 6/2003 | Shlomo et al. |
| 6,587,721 B1 | 7/2003 | Prutchi et al. |
| 6,597,952 B1 | 7/2003 | Mika et al. |
| 6,600,953 B2 | 7/2003 | Flesler et al. |
| 6,640,136 B1 | 10/2003 | Helland et al. |
| 6,662,055 B1 | 12/2003 | Prutchi |
| 6,669,693 B2 | 12/2003 | Friedman |
| 6,675,043 B1 | 1/2004 | Prutchi et al. |
| 6,684,105 B2 | 1/2004 | Cohen et al. |
| 6,694,192 B2 | 2/2004 | Policker et al. |
| 6,712,831 B1 | 3/2004 | Kaplan et al. |
| 6,725,093 B1 | 4/2004 | Ben-haim et al. |
| 6,738,655 B1 | 5/2004 | Sen et al. |
| 6,740,113 B2 | 5/2004 | Vrba |
| 6,748,271 B2 | 6/2004 | Spinelli et al. |
| 6,749,600 B1 | 6/2004 | Levy |
| 6,754,532 B1 | 6/2004 | Ferek-Petric |
| RE38,654 E | 11/2004 | Hill et al. |
| 6,832,478 B2 | 12/2004 | Anderson et al. |
| 6,850,801 B2 | 2/2005 | Kieval et al. |
| 6,882,886 B1 | 4/2005 | Witte et al. |
| 6,887,266 B2 | 5/2005 | Williams et al. |
| 6,912,419 B2 | 6/2005 | Hill et al. |
| 6,932,930 B2 | 8/2005 | Desimone et al. |
| 6,944,490 B1 | 9/2005 | Chow |
| 6,947,792 B2 | 9/2005 | Ben-haim et al. |
| 6,950,689 B1 | 9/2005 | Willis et al. |
| 6,973,350 B1 | 12/2005 | Levine et al. |
| 6,985,774 B2 | 1/2006 | Kieval et al. |
| 6,993,385 B1 | 1/2006 | Routh et al. |
| 7,018,401 B1 | 3/2006 | Hyodoh et al. |
| 7,020,523 B1 | 3/2006 | Lu et al. |
| 7,027,863 B1 | 4/2006 | Prutchi et al. |
| 7,062,318 B2 | 6/2006 | Ben-haim et al. |
| 7,072,720 B2 | 7/2006 | Puskas |
| 7,082,336 B2 | 7/2006 | Ransbury et al. |
| 7,092,753 B2 | 8/2006 | Darvish et al. |
| 7,092,759 B2 | 8/2006 | Nehls et al. |
| 7,096,070 B1 | 8/2006 | Jenkins et al. |
| 7,097,665 B2 | 8/2006 | Stack et al. |
| 7,111,627 B2 | 9/2006 | Stack et al. |
| 7,121,283 B2 | 10/2006 | Stack et al. |
| 7,141,061 B2 | 11/2006 | Williams et al. |
| 7,146,984 B2 | 12/2006 | Stack et al. |
| 7,152,607 B2 | 12/2006 | Stack et al. |
| 7,158,832 B2 | 1/2007 | Kieval et al. |
| 7,163,554 B2 | 1/2007 | Williams et al. |
| 7,167,748 B2 | 1/2007 | Ben-haim et al. |
| 7,171,263 B2 | 1/2007 | Darvish et al. |
| 7,187,970 B2 | 3/2007 | Shemer et al. |
| 7,190,997 B1 | 3/2007 | Darvish et al. |
| 7,195,594 B2 | 3/2007 | Eigler et al. |
| 7,195,637 B2 | 3/2007 | Mika |
| 7,218,963 B2 | 5/2007 | Ben-haim et al. |
| 7,231,260 B2 | 6/2007 | Wallace et al. |
| 7,260,431 B2 | 8/2007 | Libbus et al. |
| 7,277,757 B2 | 10/2007 | Casavant et al. |
| 7,277,761 B2 | 10/2007 | Shelchuk |
| 7,279,007 B2 | 10/2007 | Nikolic |
| 7,285,287 B2 | 10/2007 | Williams et al. |
| 7,295,881 B2 | 11/2007 | Cohen et al. |

(56) References Cited

U.S. PATENT DOCUMENTS

| | | |
|---|---|---|
| 7,308,303 B2 | 12/2007 | Whitehurst et al. |
| 7,310,555 B2 | 12/2007 | Ben-haim et al. |
| 7,321,793 B2 | 1/2008 | Ben Ezra et al. |
| 7,354,454 B2 | 4/2008 | Stack et al. |
| 7,363,082 B2 | 4/2008 | Ransbury et al. |
| 7,377,939 B2 | 5/2008 | Williams et al. |
| 7,389,149 B2 | 6/2008 | Rossing et al. |
| 7,412,289 B2 | 8/2008 | Malonek et al. |
| 7,431,725 B2 | 10/2008 | Stack et al. |
| 7,460,906 B2 | 12/2008 | Libbus |
| 7,460,907 B1 | 12/2008 | Darvish et al. |
| 7,486,991 B2 | 2/2009 | Libbus et al. |
| 7,499,742 B2 | 3/2009 | Bolea et al. |
| 7,509,166 B2 | 3/2009 | Libbus |
| 7,529,589 B2 | 5/2009 | Williams et al. |
| 7,542,800 B2 | 6/2009 | Libbus et al. |
| 7,547,286 B2 | 6/2009 | Choate |
| 7,561,923 B2 | 7/2009 | Libbus et al. |
| 7,616,997 B2 | 11/2009 | Kieval et al. |
| 7,617,003 B2 | 11/2009 | Caparso et al. |
| 7,617,007 B2 | 11/2009 | Williams et al. |
| 7,623,926 B2 | 11/2009 | Rossing et al. |
| 7,630,760 B2 | 12/2009 | Libbus et al. |
| 7,634,317 B2 | 12/2009 | Ben-David et al. |
| 7,643,875 B2 | 1/2010 | Heil, Jr. et al. |
| 7,647,102 B2 | 1/2010 | Routh et al. |
| 7,658,709 B2 | 2/2010 | Anderson et al. |
| 7,668,602 B2 | 2/2010 | Ben-David et al. |
| 7,676,266 B1 | 3/2010 | Kroll |
| 7,704,276 B2 | 4/2010 | Williams et al. |
| 7,706,884 B2 | 4/2010 | Libbus |
| 7,734,343 B2 | 6/2010 | Ransbury et al. |
| 7,734,348 B2 | 6/2010 | Zhang et al. |
| 7,747,335 B2 | 6/2010 | Williams |
| 7,765,000 B2 | 7/2010 | Zhang et al. |
| 7,769,446 B2 | 8/2010 | Moffitt et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,801,614 B2 | 9/2010 | Rossing et al. |
| 7,805,194 B1 | 9/2010 | Schecter |
| 7,805,203 B2 | 9/2010 | Ben-David et al. |
| 7,813,812 B2 | 10/2010 | Kieval et al. |
| 7,840,262 B2 | 11/2010 | Mika et al. |
| 7,840,271 B2 | 11/2010 | Kieval et al. |
| 7,840,282 B2 | 11/2010 | Williams et al. |
| 7,848,812 B2 | 12/2010 | Crowley et al. |
| 7,857,748 B2 | 12/2010 | Wiliams et al. |
| 7,869,881 B2 | 1/2011 | Libbus et al. |
| 7,873,413 B2 | 1/2011 | McCabe et al. |
| 7,881,782 B2 | 2/2011 | Libbus et al. |
| 7,885,709 B2 | 2/2011 | Ben-David |
| 7,885,711 B2 | 2/2011 | Ben-Ezra et al. |
| 7,890,185 B2 | 2/2011 | Cohen et al. |
| 7,892,292 B2 | 2/2011 | Stack et al. |
| 7,899,554 B2 | 3/2011 | Wiliams et al. |
| 7,904,151 B2 | 3/2011 | Ben-David et al. |
| 7,904,176 B2 | 3/2011 | Ben-Ezra et al. |
| 7,908,008 B2 | 3/2011 | Ben-David et al. |
| 7,919,162 B2 | 4/2011 | Desimone et al. |
| 7,925,352 B2 | 4/2011 | Stack et al. |
| 7,949,400 B2 | 5/2011 | Kieval et al. |
| 7,953,481 B1 | 5/2011 | Shemer et al. |
| 7,966,067 B2 | 6/2011 | Rousso et al. |
| 7,974,693 B2 | 7/2011 | Ben-David et al. |
| 8,000,793 B2 | 8/2011 | Libbus |
| 8,005,542 B2 | 8/2011 | Ben-Ezra et al. |
| 8,005,545 B2 | 8/2011 | Ben-David et al. |
| 8,014,858 B1 | 9/2011 | Ben-haim et al. |
| 8,014,874 B2 | 9/2011 | Rossing et al. |
| 8,024,050 B2 | 9/2011 | Libbus et al. |
| 8,027,724 B2 | 9/2011 | Wei et al. |
| 8,032,215 B2 | 10/2011 | Libbus et al. |
| 8,036,745 B2 | 10/2011 | Ben-David et al. |
| 8,060,197 B2 | 11/2011 | Ben-David et al. |
| 8,060,206 B2 | 11/2011 | Kieval et al. |
| 8,060,218 B2 | 11/2011 | Singh et al. |
| 8,086,314 B1 | 12/2011 | Kieval |
| 8,116,881 B2 | 2/2012 | Cohen et al. |
| 8,116,883 B2 | 2/2012 | Williams et al. |
| 8,118,751 B2 | 2/2012 | Dobak, III |
| 8,121,693 B2 | 2/2012 | Libbus |
| 8,126,560 B2 | 2/2012 | Schiener et al. |
| 8,131,373 B2 | 3/2012 | Libbus |
| 8,145,304 B2 | 3/2012 | Moffitt et al. |
| 8,150,521 B2 | 4/2012 | Crowley et al. |
| 8,152,843 B2 | 4/2012 | Williams et al. |
| 8,155,744 B2 | 4/2012 | Rezai |
| 8,175,705 B2 | 5/2012 | Libbus |
| 8,195,289 B2 | 6/2012 | Heil, Jr. et al. |
| 8,195,290 B2 | 6/2012 | Brockway et al. |
| 8,204,591 B2 | 6/2012 | Ben-David et al. |
| 8,204,596 B2 | 6/2012 | Ransbury et al. |
| 8,206,456 B2 | 6/2012 | Stack et al. |
| 8,224,444 B2 | 7/2012 | Ben-David et al. |
| 8,229,564 B2 | 7/2012 | Rezai |
| 8,239,037 B2 | 8/2012 | Glenn et al. |
| 8,239,045 B2 | 8/2012 | Ransbury et al. |
| 8,244,355 B2 | 8/2012 | Bennett et al. |
| 8,249,706 B2 | 8/2012 | Koh |
| 8,260,416 B2 | 9/2012 | Ben-haim et al. |
| 8,271,099 B1 | 9/2012 | Swanson |
| 8,290,595 B2 | 10/2012 | Kieval et al. |
| 8,301,247 B2 | 10/2012 | Ben-haim et al. |
| 8,306,616 B2 | 11/2012 | Ben-haim et al. |
| 8,306,617 B2 | 11/2012 | Ben-haim et al. |
| 8,311,629 B2 | 11/2012 | Ben-haim et al. |
| 8,311,633 B2 | 11/2012 | Ransbury et al. |
| 8,321,013 B2 | 11/2012 | Darvish et al. |
| 8,326,416 B2 | 12/2012 | Mika et al. |
| 8,335,571 B2 | 12/2012 | Singh et al. |
| 8,352,031 B2 | 1/2013 | Rousso et al. |
| 8,369,954 B2 | 2/2013 | Stack et al. |
| 8,372,325 B2 | 2/2013 | Williams et al. |
| 8,386,053 B2 | 2/2013 | Kornet |
| 8,386,056 B2 | 2/2013 | Ben-David et al. |
| 8,401,672 B2 | 3/2013 | Libbus et al. |
| 8,406,864 B2 | 3/2013 | Rousso et al. |
| 8,406,877 B2 | 3/2013 | Smith et al. |
| 8,412,326 B2 | 4/2013 | Arcot-Krishnamurthy et al. |
| 8,417,354 B2 | 4/2013 | Zhang et al. |
| 8,423,134 B2 | 4/2013 | Buschman et al. |
| 8,428,730 B2 | 4/2013 | Stack |
| 8,437,867 B2 | 5/2013 | Murney et al. |
| 8,452,398 B2 | 5/2013 | Libbus et al. |
| 8,473,076 B2 | 6/2013 | Libbus et al. |
| 8,498,703 B2 | 7/2013 | Spinelli et al. |
| 8,538,535 B2 | 9/2013 | Gross et al. |
| 8,548,583 B2 | 10/2013 | Rousso et al. |
| 8,565,896 B2 | 10/2013 | Ben-David et al. |
| 8,571,651 B2 | 10/2013 | Ben-Ezra et al. |
| 8,571,653 B2 | 10/2013 | Ben-David et al. |
| 8,583,236 B2 | 11/2013 | Kieval et al. |
| 8,606,359 B2 | 12/2013 | Rossing et al. |
| 8,609,082 B2 | 12/2013 | Ben-David et al. |
| 8,615,294 B2 | 12/2013 | Ben-David et al. |
| 8,620,426 B2 | 12/2013 | Moffitt |
| 8,626,290 B2 | 1/2014 | Dagan et al. |
| 8,626,299 B2 | 1/2014 | Gross et al. |
| 8,634,921 B2 | 1/2014 | Chavan et al. |
| 8,639,332 B2 | 1/2014 | Kuhn et al. |
| 8,655,444 B2 | 2/2014 | Ben-haim et al. |
| 8,682,430 B2 | 3/2014 | Libbus et al. |
| 8,682,434 B2 | 3/2014 | Libbus |
| 8,706,230 B2 | 4/2014 | Rousso et al. |
| 8,712,531 B2 | 4/2014 | Kieval et al. |
| 8,718,789 B2 | 5/2014 | Bolea et al. |
| 8,725,250 B2 | 5/2014 | Brockway et al. |
| 8,755,907 B2 | 6/2014 | Kieval et al. |
| 8,764,817 B2 | 7/2014 | Sheldon |
| 8,771,337 B2 | 7/2014 | Williams et al. |
| 8,784,354 B2 | 7/2014 | Stack et al. |
| 8,784,500 B2 | 7/2014 | Stack et al. |
| 8,788,066 B2 | 7/2014 | Cates et al. |

(56) References Cited

U.S. PATENT DOCUMENTS

| | | |
|---|---|---|
| 8,798,738 B2 | 8/2014 | Machado et al. |
| 8,805,501 B2 | 8/2014 | Libbus |
| 8,818,501 B2 | 8/2014 | Machado et al. |
| 8,825,152 B2 | 9/2014 | Shemer et al. |
| 8,838,246 B2 | 9/2014 | Kieval |
| 8,855,783 B2 | 10/2014 | Dagan et al. |
| 8,880,190 B2 | 11/2014 | Kieval et al. |
| 8,886,340 B2 | 11/2014 | Williams et al. |
| 8,901,878 B2 | 12/2014 | Prutchi et al. |
| 8,906,286 B2 | 12/2014 | Desimone et al. |
| 8,918,172 B2 | 12/2014 | Moffitt et al. |
| 8,929,990 B2 | 1/2015 | Moffitt et al. |
| 8,934,956 B2 | 1/2015 | Glenn et al. |
| 8,934,968 B2 | 1/2015 | Whitehurst et al. |
| 8,958,872 B2 | 2/2015 | Ben-haim et al. |
| 8,972,015 B2 | 3/2015 | Stack et al. |
| 8,977,353 B2 | 3/2015 | Rousso et al. |
| 8,983,601 B2 | 3/2015 | Fukamachi et al. |
| 9,005,100 B2 | 4/2015 | Gnanashanmugam et al. |
| 9,005,106 B2 | 4/2015 | Gross et al. |
| 9,011,751 B2 | 4/2015 | Williams et al. |
| 9,031,650 B2 | 5/2015 | McCabe et al. |
| 9,031,669 B2 | 5/2015 | Zhang et al. |
| 9,044,609 B2 | 6/2015 | Bolea et al. |
| 9,067,071 B2 | 6/2015 | Sanders et al. |
| 9,126,048 B2 | 9/2015 | Ransbury et al. |
| 9,149,639 B2 | 10/2015 | Zhang et al. |
| 9,168,094 B2 | 10/2015 | Lee et al. |
| 9,180,035 B2 | 11/2015 | Stack et al. |
| 9,186,514 B2 | 11/2015 | Ben-haim et al. |
| 9,216,289 B2 | 12/2015 | Libbus et al. |
| 9,248,038 B2 | 2/2016 | Stack et al. |
| 9,289,618 B1 | 3/2016 | Ben-haim et al. |
| 9,446,240 B2 | 9/2016 | Masson et al. |
| 9,480,790 B2 | 11/2016 | Machado et al. |
| 9,494,960 B2 | 11/2016 | Weerakoon et al. |
| 9,504,833 B2 | 11/2016 | Kramer et al. |
| 9,511,229 B2 | 12/2016 | Bradley |
| 9,517,350 B2 | 12/2016 | Ternes et al. |
| 9,545,512 B2 | 1/2017 | Williams et al. |
| 9,597,515 B2 | 3/2017 | Rockweiler et al. |
| 9,610,012 B2 | 4/2017 | Bardy |
| 9,622,665 B2 | 4/2017 | Zhang et al. |
| 9,623,252 B2 | 4/2017 | Sathaye et al. |
| 9,636,503 B2 | 5/2017 | Mokelke et al. |
| 9,656,089 B2 | 5/2017 | Yip et al. |
| 9,687,653 B2 | 6/2017 | Woods et al. |
| 9,707,076 B2 | 7/2017 | Stack et al. |
| 9,717,899 B2 | 8/2017 | Kuzma et al. |
| 9,731,135 B2 | 8/2017 | Arcot-Krishnamurthy et al. |
| 9,737,228 B2 | 8/2017 | Mahajan et al. |
| 9,782,591 B2 | 10/2017 | Kramer et al. |
| 9,814,883 B2 | 11/2017 | Marnfeldt et al. |
| 9,827,413 B2 | 11/2017 | Barker et al. |
| 9,833,608 B2 | 12/2017 | Masson |
| 9,844,453 B2 | 12/2017 | Stack et al. |
| 9,848,795 B2 | 12/2017 | Marecki et al. |
| 9,849,290 B2 | 12/2017 | Zhao et al. |
| 9,855,317 B2 | 1/2018 | Bright |
| 9,861,435 B2 | 1/2018 | Richardson et al. |
| 9,878,150 B2 | 1/2018 | Machado et al. |
| 9,884,182 B2 | 2/2018 | Ransbury et al. |
| 9,895,242 B2 | 2/2018 | Sheldon et al. |
| 10,172,549 B2 | 1/2019 | Waldhauser et al. |
| 10,188,343 B2 | 1/2019 | Goedeke et al. |
| 10,322,000 B2 | 6/2019 | Orth et al. |
| 10,448,884 B2 | 10/2019 | Goedeke et al. |
| 10,493,278 B2 | 12/2019 | Waldhauser et al. |
| 10,576,273 B2 | 3/2020 | Goedeke et al. |
| 10,639,478 B2 | 5/2020 | Cuchiara et al. |
| 10,660,698 B2 | 5/2020 | Willard et al. |
| 10,722,716 B2 | 7/2020 | Waldhauser et al. |
| 10,729,911 B2 | 8/2020 | Yip et al. |
| 10,857,352 B2 | 12/2020 | Ransbury et al. |
| 10,894,160 B2 | 1/2021 | Waldhauser et al. |
| 10,905,873 B2 | 2/2021 | Machado et al. |
| 10,952,665 B2 | 3/2021 | Goedeke et al. |
| 11,033,741 B2 | 6/2021 | Cuchiara et al. |
| 11,065,438 B2 | 7/2021 | Stack et al. |
| 11,077,298 B2 | 8/2021 | Waldhauser et al. |
| 11,129,603 B2 | 9/2021 | Stack et al. |
| 11,185,699 B2 | 11/2021 | Masson et al. |
| 11,202,904 B2 | 12/2021 | Masson |
| 11,229,398 B2 | 1/2022 | Christian et al. |
| 2002/0087192 A1 | 7/2002 | Barrett et al. |
| 2003/0045909 A1 | 3/2003 | Gross et al. |
| 2003/0052775 A1* | 3/2003 | Shambroom ............ A61B 5/30 600/300 |
| 2003/0114739 A1 | 6/2003 | Fuimaono et al. |
| 2003/0114878 A1 | 6/2003 | Diederich et al. |
| 2003/0216792 A1 | 11/2003 | Levin et al. |
| 2003/0233099 A1 | 12/2003 | Danaek et al. |
| 2004/0097965 A1 | 5/2004 | Gardeski et al. |
| 2004/0098090 A1 | 5/2004 | Williams et al. |
| 2004/0143254 A1 | 7/2004 | Vanney et al. |
| 2004/0172079 A1 | 9/2004 | Chinchoy |
| 2004/0172094 A1 | 9/2004 | Cohen et al. |
| 2004/0181136 A1 | 9/2004 | McDaniel et al. |
| 2004/0193231 A1 | 9/2004 | David et al. |
| 2004/0215233 A1 | 10/2004 | Kaplan et al. |
| 2004/0260375 A1 | 12/2004 | Zhang et al. |
| 2005/0004638 A1 | 1/2005 | Cross, Jr. |
| 2005/0065553 A1 | 3/2005 | Ben Ezra et al. |
| 2005/0119752 A1 | 6/2005 | Williams et al. |
| 2005/0142315 A1 | 6/2005 | Desimone et al. |
| 2005/0154321 A1 | 7/2005 | Wolinsky et al. |
| 2005/0187556 A1 | 8/2005 | Stack et al. |
| 2005/0187586 A1 | 8/2005 | David et al. |
| 2005/0187615 A1 | 8/2005 | Williams et al. |
| 2005/0197675 A1 | 9/2005 | David et al. |
| 2005/0247320 A1 | 11/2005 | Stack et al. |
| 2005/0251239 A1 | 11/2005 | Wallace et al. |
| 2005/0267542 A1 | 12/2005 | David et al. |
| 2005/0271794 A1 | 12/2005 | Desimone et al. |
| 2005/0273146 A1 | 12/2005 | Desimone et al. |
| 2006/0058597 A1 | 3/2006 | Machado et al. |
| 2006/0074453 A1 | 4/2006 | Kieval et al. |
| 2006/0085046 A1 | 4/2006 | Rezai et al. |
| 2006/0089694 A1 | 4/2006 | Zhang et al. |
| 2006/0100668 A1 | 5/2006 | Ben-David et al. |
| 2006/0116737 A1 | 6/2006 | Libbus |
| 2006/0206159 A1 | 9/2006 | Moffitt et al. |
| 2006/0229677 A1 | 10/2006 | Moffitt et al. |
| 2006/0259084 A1 | 11/2006 | Zhang et al. |
| 2006/0259085 A1 | 11/2006 | Zhang et al. |
| 2007/0023951 A1 | 2/2007 | Williams et al. |
| 2007/0027527 A1 | 2/2007 | Williams et al. |
| 2007/0060932 A1 | 3/2007 | Stack et al. |
| 2007/0093803 A1 | 4/2007 | Dalbec et al. |
| 2007/0135875 A1 | 6/2007 | Demarais et al. |
| 2007/0255364 A1 | 11/2007 | Gerber et al. |
| 2008/0004618 A1 | 1/2008 | Johnson et al. |
| 2008/0015659 A1 | 1/2008 | Zhang et al. |
| 2008/0046016 A1 | 2/2008 | Ben-David et al. |
| 2008/0046051 A1 | 2/2008 | Skubitz et al. |
| 2008/0082137 A1 | 4/2008 | Kieval et al. |
| 2008/0086182 A1 | 4/2008 | Ben-David et al. |
| 2008/0091240 A1 | 4/2008 | Ben-David et al. |
| 2008/0091241 A1 | 4/2008 | Ben-Ezra et al. |
| 2008/0091245 A1 | 4/2008 | Ben-Ezra et al. |
| 2008/0119898 A1 | 5/2008 | Ben-David et al. |
| 2008/0125819 A1 | 5/2008 | Ben-David et al. |
| 2008/0125825 A1 | 5/2008 | Ben-Ezra et al. |
| 2008/0125827 A1 | 5/2008 | Ben-David et al. |
| 2008/0125843 A1 | 5/2008 | Ben-David et al. |
| 2008/0132964 A1 | 6/2008 | Cohen et al. |
| 2008/0132983 A1 | 6/2008 | Cohen et al. |
| 2008/0140141 A1 | 6/2008 | Ben-David et al. |
| 2008/0147140 A1 | 6/2008 | Ternes et al. |
| 2008/0161894 A1 | 7/2008 | Ben-David et al. |
| 2008/0167693 A1 | 7/2008 | Kieval et al. |
| 2008/0177338 A1 | 7/2008 | Ben-David et al. |
| 2008/0215008 A1 | 9/2008 | Nance et al. |
| 2008/0275349 A1 | 11/2008 | Halperin et al. |

(56) References Cited

U.S. PATENT DOCUMENTS

| | | |
|---|---|---|
| 2008/0275514 A1 | 11/2008 | Ben-David et al. |
| 2008/0312711 A1 | 12/2008 | Struble |
| 2009/0012542 A1 | 1/2009 | N'diaye et al. |
| 2009/0012546 A1 | 1/2009 | N'diaye et al. |
| 2009/0018596 A1 | 1/2009 | Kieval |
| 2009/0022078 A1 | 1/2009 | Zhang et al. |
| 2009/0096137 A1 | 4/2009 | Williams et al. |
| 2009/0105823 A1 | 4/2009 | Williams et al. |
| 2009/0163912 A1 | 6/2009 | Wang et al. |
| 2009/0222073 A1 | 9/2009 | Flowers et al. |
| 2009/0228078 A1 | 9/2009 | Zhang et al. |
| 2009/0240248 A1 | 9/2009 | Deford et al. |
| 2009/0276022 A1 | 11/2009 | Burnes et al. |
| 2009/0281608 A1 | 11/2009 | Foster |
| 2010/0023088 A1 | 1/2010 | Stack et al. |
| 2010/0069768 A1 | 3/2010 | Min et al. |
| 2010/0191088 A1 | 7/2010 | Anderson et al. |
| 2010/0222832 A1 | 9/2010 | Zhang et al. |
| 2010/0280366 A1 | 11/2010 | Arne et al. |
| 2011/0004198 A1 | 1/2011 | Hoch |
| 2011/0106199 A1 | 5/2011 | McCabe et al. |
| 2011/0118726 A1 | 5/2011 | de la Rama et al. |
| 2011/0153030 A1 | 6/2011 | Stack et al. |
| 2011/0160790 A1 | 6/2011 | Stegemann et al. |
| 2012/0029510 A1 | 2/2012 | Haverkost |
| 2012/0035436 A1 | 2/2012 | Kirchner et al. |
| 2012/0101413 A1 | 4/2012 | Beetel et al. |
| 2012/0197141 A1 | 8/2012 | Vanney et al. |
| 2012/0232563 A1 | 9/2012 | Williams et al. |
| 2012/0253280 A1 | 10/2012 | Pantin et al. |
| 2012/0283585 A1 | 11/2012 | Werneth et al. |
| 2012/0303086 A1 | 11/2012 | Ben-David et al. |
| 2012/0310304 A1 | 12/2012 | Brockway et al. |
| 2013/0012863 A1 | 1/2013 | Stack et al. |
| 2013/0102869 A1 | 4/2013 | Kordis et al. |
| 2013/0110208 A1 | 5/2013 | Inagaki et al. |
| 2013/0172715 A1 | 7/2013 | Just et al. |
| 2013/0218221 A1 | 8/2013 | Zhang et al. |
| 2013/0226272 A1 | 8/2013 | Cattaneo et al. |
| 2013/0253616 A1 | 9/2013 | Libbus et al. |
| 2013/0289358 A1 | 10/2013 | Meisky et al. |
| 2013/0289686 A1 | 10/2013 | Masson et al. |
| 2013/0331919 A1 | 12/2013 | Zhang et al. |
| 2013/0338748 A1 | 12/2013 | Dagan |
| 2014/0012242 A1 | 1/2014 | Lee et al. |
| 2014/0046407 A1 | 2/2014 | Ben-Ezra et al. |
| 2014/0052208 A1 | 2/2014 | Ransbury et al. |
| 2014/0074148 A1 | 3/2014 | Glenn et al. |
| 2014/0114377 A1 | 4/2014 | Dagan et al. |
| 2014/0128750 A1 | 5/2014 | Ransbury et al. |
| 2014/0148883 A1 | 5/2014 | Stack et al. |
| 2014/0171783 A1* | 6/2014 | Schmidt ............... A61B 5/7285 600/413 |
| 2014/0172006 A1 | 6/2014 | Stack et al. |
| 2014/0214135 A1 | 7/2014 | Ben-David et al. |
| 2014/0221975 A1 | 8/2014 | Gnanashanmugam et al. |
| 2014/0222031 A1 | 8/2014 | Stack et al. |
| 2014/0222125 A1 | 8/2014 | Glenn et al. |
| 2014/0277235 A1 | 9/2014 | An et al. |
| 2014/0277281 A1 | 9/2014 | Grandhe |
| 2014/0324115 A1 | 10/2014 | Ziegler et al. |
| 2015/0018908 A1 | 1/2015 | Williams et al. |
| 2015/0025532 A1 | 1/2015 | Hanson et al. |
| 2015/0039058 A1 | 2/2015 | Masson et al. |
| 2015/0066006 A1 | 3/2015 | Srivastava |
| 2015/0066133 A1 | 3/2015 | Desimone et al. |
| 2015/0105645 A1 | 4/2015 | Subramaniam et al. |
| 2015/0134019 A1 | 5/2015 | Moffitt et al. |
| 2015/0142011 A1 | 5/2015 | Cates et al. |
| 2015/0148696 A1* | 5/2015 | Lall ..................... A61B 5/35 600/510 |
| 2015/0150508 A1 | 6/2015 | Glenn et al. |
| 2015/0151121 A1 | 6/2015 | Dagan et al. |
| 2015/0157777 A1 | 6/2015 | Tuval et al. |
| 2015/0164662 A1 | 6/2015 | Tuval |
| 2015/0238763 A1 | 8/2015 | Bolea et al. |
| 2015/0306395 A1 | 10/2015 | Libbus et al. |
| 2015/0328448 A1 | 11/2015 | Richter et al. |
| 2016/0022890 A1 | 1/2016 | Schwammenthal et al. |
| 2016/0051321 A1 | 2/2016 | Salahieh et al. |
| 2016/0051741 A1 | 2/2016 | Schwammenthal et al. |
| 2016/0174864 A1 | 6/2016 | Levin et al. |
| 2016/0256112 A1 | 9/2016 | Brockway et al. |
| 2017/0001015 A1 | 1/2017 | Marnfeldt et al. |
| 2017/0027458 A1 | 2/2017 | Glover et al. |
| 2017/0065818 A1 | 3/2017 | Ransbury et al. |
| 2017/0143227 A1 | 5/2017 | Marecki et al. |
| 2017/0189106 A1 | 7/2017 | Schuler et al. |
| 2017/0189642 A1 | 7/2017 | Masson et al. |
| 2017/0224415 A1 | 8/2017 | Dong et al. |
| 2017/0224999 A1 | 8/2017 | Yip et al. |
| 2017/0258337 A1 | 9/2017 | Libbus et al. |
| 2017/0291023 A1 | 10/2017 | Kuzma et al. |
| 2017/0296086 A1 | 10/2017 | Ternes et al. |
| 2017/0312525 A1 | 11/2017 | Masson et al. |
| 2017/0325881 A1 | 11/2017 | Richardson et al. |
| 2018/0050190 A1 | 2/2018 | Masson |
| 2018/0116678 A1 | 5/2018 | Melanson et al. |
| 2018/0214696 A1 | 8/2018 | Cuchiara et al. |
| 2018/0214697 A1 | 8/2018 | Cuchiara et al. |
| 2018/0214698 A1 | 8/2018 | Cuchiara et al. |
| 2018/0236220 A1 | 8/2018 | Glenn et al. |
| 2018/0369589 A1 | 12/2018 | Schouenborg et al. |
| 2019/0186702 A1 | 6/2019 | Masson |
| 2019/0247034 A1 | 8/2019 | Stack et al. |
| 2019/0262148 A1 | 8/2019 | Orth et al. |
| 2019/0374778 A1 | 12/2019 | Masson et al. |
| 2020/0086125 A1 | 3/2020 | Parramon et al. |
| 2020/0101292 A1 | 4/2020 | Waldhauser et al. |
| 2020/0164204 A1 | 5/2020 | Masson et al. |
| 2020/0187805 A1 | 6/2020 | Purcell et al. |
| 2020/0187879 A1 | 6/2020 | Purcell |
| 2020/0194771 A1 | 6/2020 | Purcell |
| 2020/0197692 A1 | 6/2020 | Goedeke et al. |
| 2020/0206511 A1 | 7/2020 | Goedeke et al. |
| 2020/0206512 A1 | 7/2020 | Masson et al. |
| 2020/0214627 A1 | 7/2020 | Christian et al. |
| 2020/0261151 A1 | 8/2020 | Willard et al. |
| 2020/0269052 A1 | 8/2020 | Masson et al. |
| 2020/0282217 A1 | 9/2020 | Masson et al. |
| 2020/0360694 A1 | 11/2020 | Waldhauser et al. |
| 2021/0154470 A1 | 5/2021 | Machado et al. |
| 2021/0204871 A1 | 7/2021 | Goedeke et al. |
| 2021/0220131 A1 | 7/2021 | Stack et al. |
| 2021/0275816 A1 | 9/2021 | Cuchiara et al. |
| 2021/0370055 A1 | 12/2021 | Waldhauser et al. |
| 2021/0370068 A1 | 12/2021 | Waldhauser et al. |

FOREIGN PATENT DOCUMENTS

| | | | |
|---|---|---|---|
| CN | 103315806 | 9/2013 | |
| EP | 1 871 469 | 10/2013 | |
| EP | 2904965 | 8/2015 | |
| EP | 2 316 525 | 1/2016 | |
| EP | 3 194 007 | 7/2017 | |
| EP | 2 731 671 | 4/2019 | |
| EP | 2 701 795 | 12/2020 | |
| JP | 2001-505450 | 4/2001 | |
| JP | 2004-160219 | 6/2004 | |
| JP | 2008-526456 | 7/2008 | |
| JP | 2009-508594 | 3/2009 | |
| JP | 2011-147791 | 8/2011 | |
| WO | WO 1994/007412 | 4/1994 | |
| WO | WO 1997/024983 | 7/1997 | |
| WO | WO-9852463 A1 * | 11/1998 | ......... A61B 5/04017 |
| WO | WO 2005/041748 | 5/2005 | |
| WO | WO 2006/007048 | 1/2006 | |
| WO | WO 2006/058253 | 6/2006 | |
| WO | WO 2007/052341 | 5/2007 | |
| WO | WO 2008/054448 | 5/2008 | |
| WO | WO 2009/135083 | 11/2009 | |
| WO | WO 2009/135138 | 11/2009 | |
| WO | WO 2011/075328 | 6/2011 | |
| WO | WO 2012/068273 | 5/2012 | |

(56) References Cited

FOREIGN PATENT DOCUMENTS

| WO | WO 2012/145285 | 10/2012 |
|---|---|---|
| WO | WO 2012/149511 | 11/2012 |
| WO | WO 2015/179634 | 11/2015 |
| WO | WO 2016/040037 | 3/2016 |
| WO | WO 2016/049038 | 3/2016 |
| WO | WO 2016/111940 | 7/2016 |
| WO | WO 2016/195477 | 12/2016 |
| WO | WO 2017/156039 | 9/2017 |
| WO | WO 2018/060394 | 4/2018 |
| WO | WO 2019/055434 | 3/2019 |
| WO | WO 2020/036886 | 2/2020 |
| WO | WO 2020/227234 | 11/2020 |
| WO | WO 2021/257399 | 12/2021 |

OTHER PUBLICATIONS

Casadei, "Vagal control of myocardial. . . in humans," The Physiological Society (Mar. 2001): 817-823.
De Ferrari et al., "Vagus nerve stimulation . . . future directions," Heart Fail Rev. (2011) 16: 195-203.
Fornell, "Multi-Electrode RF Balloon Efficient for Acute Pulmonary Vein Isolation", Ablation Systems, May 17, 2017, http://www.dicardiology.com/article/multi-electrode-rf-balloon-efficient-acute-pulmonary-vein-isolation?sthash.wVTUprlW.mjjo, downloaded on Oct. 30, 2017.
Karamanoglu, "A System for Analysis of Arterial Blood Pressure Waveforms in Humans", Computers and Biomedical Research, 1997, vol. 30, pp. 244-255.
Karamanoglu et al., "Estimation of cardiac output in patients with congestive heart failure by analysis of right ventricular pressure waveforms", Biomedical Engineering Online, 2011, vol. 10, No. 36.
Karamanoglu et al., "Right Ventricular Pressure Waveform and Wave Reflection Analysis in Patients With Pulmonary Arterial Hypertension", Chest Jour., Jul. 2007, vol. 132, No. 1, pp. 37-43.
Klein et al., "Vagus nerve stimulation . . . heart failure," Cardiology Journal (2010) 17 (6): 638-643.
Koizumi et al., "Functional significance of coactivation . . . ," National Academy of Sciences (Mar. 1982) 79 (6): 2116-2120.
Lawo et al., "Electrical Signals Applied During the Absolute Refractory Period", JACC, Dec. 20, 2005, vol. 46, No. 21, pp. 2229-2236.
Meyer et al., "Augmentation of left ventricular . . . ," Americ. Heart Assoc. (2010): 1286-1294.
Murphy, "Preliminary observations of the effects of simulation of . . . in man," CA Journal of Phys. and Pharmac (Jun. 1985). 63 (6): 649-655.
Randall et al., "Regional cardiac distribution . . . ," Federation Proceedings (Jul.-Aug. 1972) 31 (4): 1199-1208.
Randall, "Augmentor action to the sympathetic . . . ," Journal of Applied Physiology (Jul. 1960) 15 (4): 629-631.
Rudski et al., "Guidelines for the Echocardiographic Assessment of the Right Heart in Adults: A Report from the American Society of Echocardiography", J Am Soc Echocardiogr, 2010, vol. 23, pp. 685-713.
Triposkiadis et al., "Sympathetic nervous . . . failure," Journal of Amer. Coll. of Cardiology (Nov. 3, 2009) 54 (19): 1747-1762.
Zarse, "Selective increase . . . sympathetic tone," Journal of Amer. Coll. of Cardiology (2005) 46 (7): 1354-1359.
International Search Report and Written Opinion issued in PCT Application No. PCT/US2020/031358, in 16 pages.
U.S. Appl. No. 11/951,285, filed Dec. 5, 2007, Methods and Systems for Treating Acute Heart Failure by Neuromodulation.
U.S. Appl. No. 12/185,473, (U.S. Pat. No. 8,818,501), filed Aug. 4, 2008 (Aug. 26, 2014), Methods and Systems for Treating Acute Heart Failure by Neuromodulation.
U.S. Appl. No. 13/654,525, (U.S. Pat. No. 8,798,738), filed Oct. 18, 2012 (Aug. 5, 2014), Methods and Systems for Treating Acute Heart Failure by Neuromodulation.
U.S. Appl. No. 14/085,311, (U.S. Pat. No. 9,480,790), filed Nov. 20, 2013 (Nov. 1, 2016), Methods and Sytems for Treating Acute Heart Failure by Neuromodulation.
U.S. Appl. No. 15/334,121, (U.S. Pat. No. 9,878,150), filed Oct. 25, 2016 (Jan. 30, 2018), Methods and Systems for Increasing Heart Contractility by Neuromodulation.
U.S. Appl. No. 15/879,694 (U.S. Pat. No. 10,905,873), filed Jan. 25, 2018 (Feb. 2, 2021), Methods and Systems for Increasing Heart Contractility by Neuromodulation.
U.S. Appl. No. 17/248,634, filed Feb. 1, 2021, Methods and Systems for Treating Acute Heart Failure by Neuromodulation.
U.S. Appl. No. 15/357,510 (U.S. Pat. No. 10,576,273), filed Nov. 21, 2016 (Mar. 3, 2020), Catheter and Catheter System for Electrical Neuromodulation.
U.S. Appl. No. 16/804,500, filed Feb. 28, 2020, Catheter and Catheter System for Electrical Neuromodulation.
U.S. Appl. No. 15/446,872, (U.S. Pat. No. 10,894,160), filed Mar. 1, 2017 (Jan. 19, 2021), Catheter and Electrode Systems for Electrical Neuromodulation.
U.S. Appl. No. 17/148,961, filed Jan. 14, 2021, Catheter and Electrode Sytems for Electrical Neuromodulation.
U.S. Appl. No. 15/446,881 (U.S. Pat. No. 10,722,716), filed Mar. 1, 2017 (Jul. 28, 2020), Methods for Electrical Neuromodulation of the Heart.
U.S. Appl. No. 16/937,932, filed Jul. 24, 2020, Methods for Electrical Neuromodulation of the Heart.
U.S. Appl. No. 15/540,161 (U.S. Pat. No. 10,493,278), filed Jun. 27, 2017 (Dec. 3, 2019), Cardiac Modulation Facilitation Methods and Systems.
U.S. Appl. No. 16/700,091, filed Dec. 2, 2019, Systems and Methods for Facilitating Therapeutic Neuromodulation.
U.S. Appl. No. 15/892,135 (U.S. Pat. No. 10,448,884), filed Feb. 8, 2018 (Oct. 22, 2019), Method of Reducing Duty Cycle During Neurostimulation Treatment.
U.S. Appl. No. 15/892,199 (U.S. Pat. No. 10,188,343), filed Feb. 8, 2018 (Jan. 29, 2019), Methods of Monitoring Effects of Neurostimulation.
U.S. Appl. No. 15/893,038 (U.S. Pat. No. 10,172,549), filed Feb. 9, 2018 (Jan. 8, 2019), Methods of Facilitating Positioning of Electrodes.
U.S. Appl. No. 16/259,306 (U.S. Pat. No. 10,952,665), filed Jan. 28, 2019 (Mar. 23, 2021), Neurostimulation Devices and Methods.
U.S. Appl. No. 16/658,618, filed Oct. 21, 2019, Methods of Reducing Duty Cycle During Neurostimulation Treatment.
U.S. Appl. No. 17/249,960, filed Mar. 19, 2021, Neurostimulation Devices and Methods.
U.S. Appl. No. 16/816,681, filed Mar. 12, 2020, Neurostimulation Systems and Methods for Affecting Cardiac Contractility.
U.S. Appl. No. 17/018,887 (U.S. Pat. No. 11,077,298), filed Sep. 11, 2020 (Aug. 3, 2021), Partially Woven Expandable Members.
U.S. Appl. No. 17/391,316, filed Aug. 2, 2021, Systems and Methods for Affecting Cardiac Contractility and/or Relaxation.

* cited by examiner

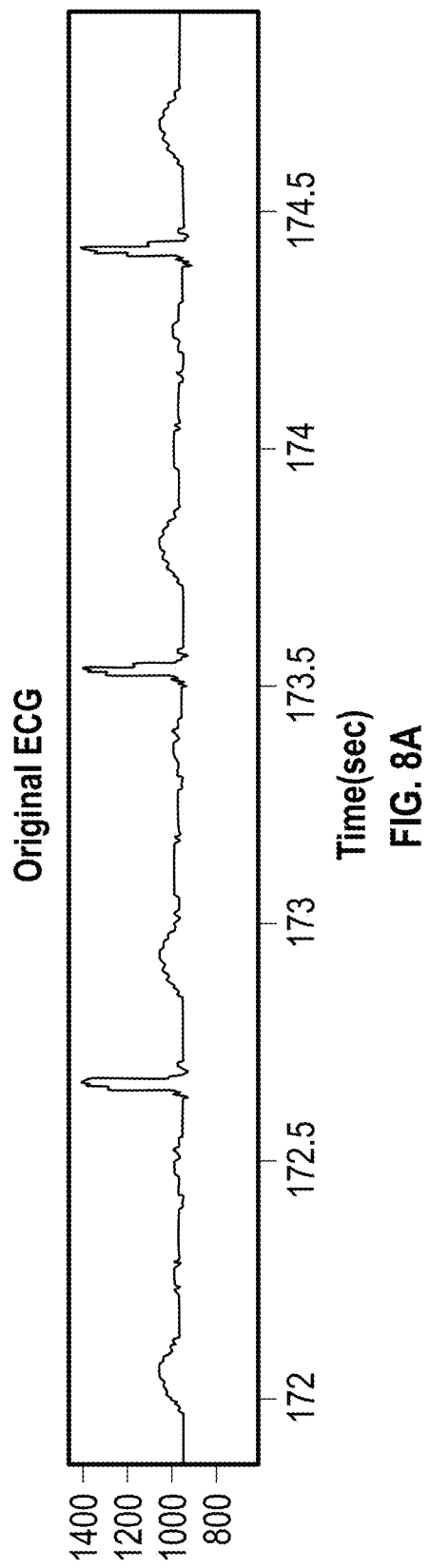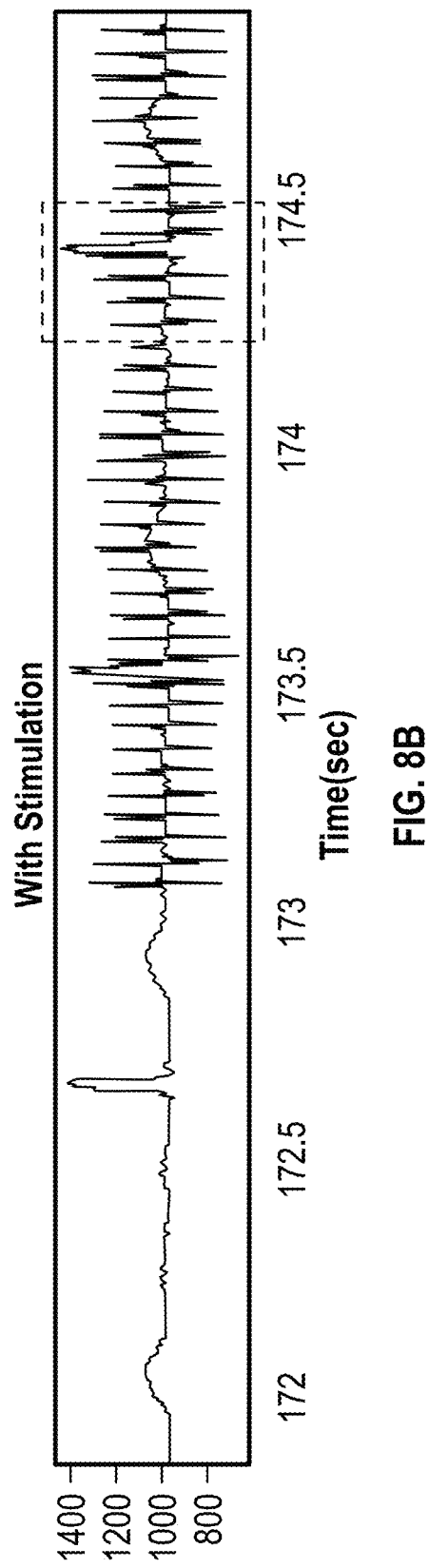
FIG. 8A
FIG. 8B

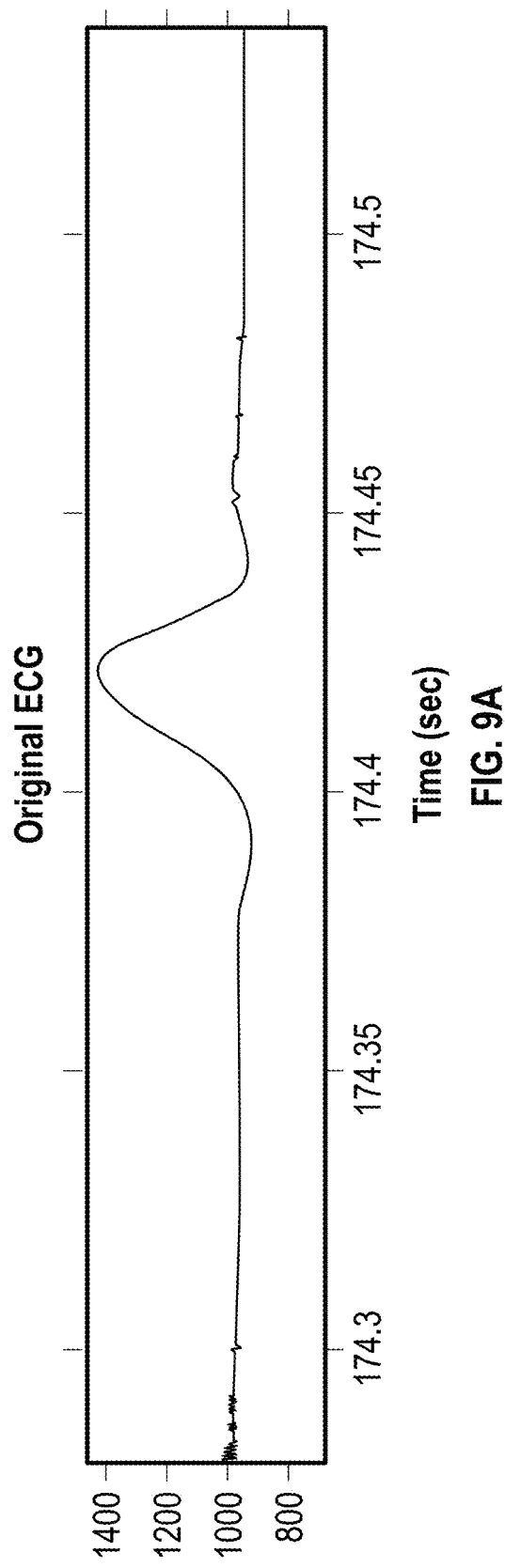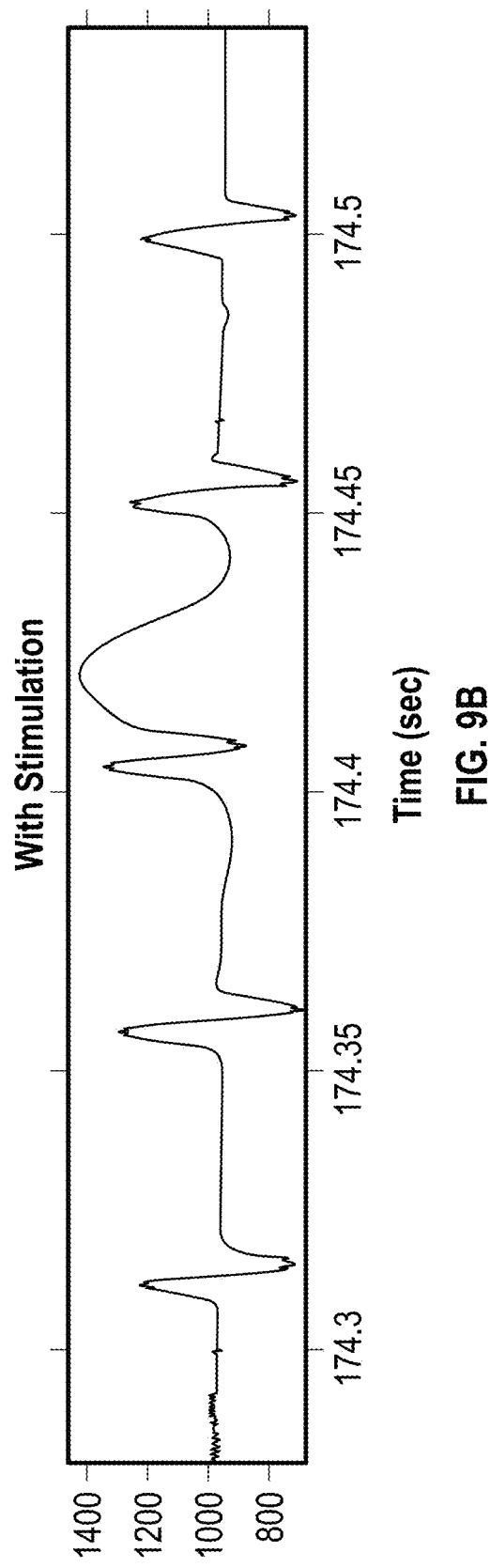

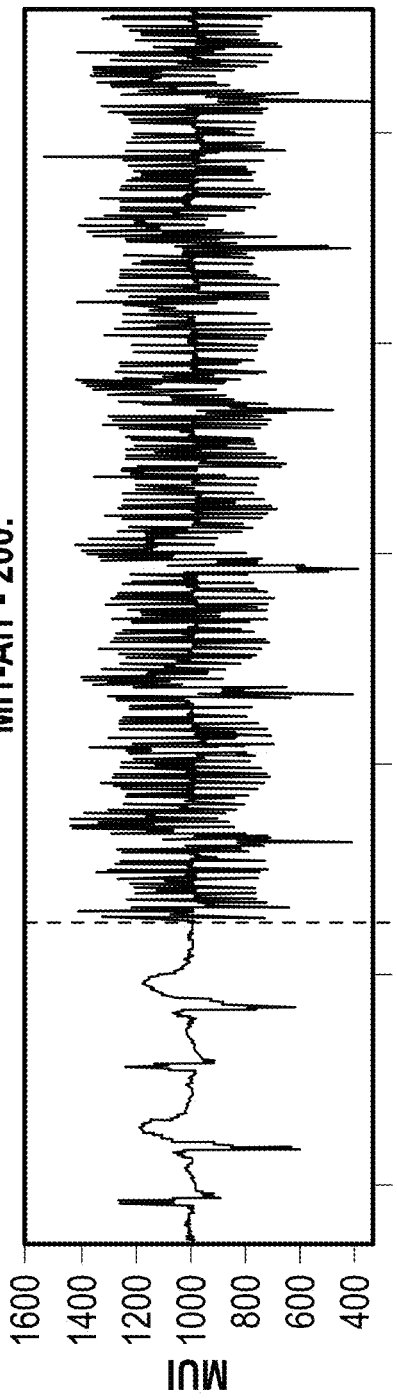
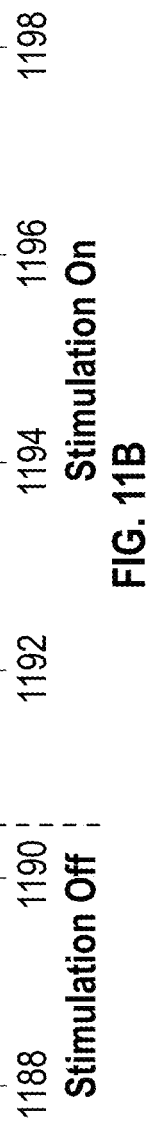
FIG. 11A
FIG. 11B

SYSTEMS AND METHODS FOR DENOISING PHYSIOLOGICAL SIGNALS DURING ELECTRICAL NEUROMODULATION

PRIORITY APPLICATIONS

This application is a continuation of International PCT Application No. PCT/US2020/031358 filed May 4, 2020, which claims priority to U.S. Provisional Application No. 62/843,772, filed May 6, 2019, the entire content of each of which is incorporated herein by reference.

FIELD

The present disclosure relates generally to methods and systems for denoising (e.g., removing unwanted noise or interference) from a display of a physiological signal (e.g., bio-signals obtained from ECG, EEG, EKG sensors). Such denoising may be performed during application of electromagnetic energy (e.g., electrical stimulation of nerves). The field also relates to methods and systems for facilitating electrical stimulation of one or more nerves in and around the heart or other organs or tissue without significantly affecting normal operation of patient monitors (e.g., during times when electrical stimulation is not being applied).

BACKGROUND

Acute heart failure is a cardiac condition in which a problem with the structure or function of the heart impairs its ability to supply sufficient blood flow to meet the body's needs. The condition impairs quality of life and is a leading cause of hospitalizations and mortality in the western world. Treating acute heart failure is typically aimed at removal of precipitating causes, prevention of deterioration in cardiac function, and control of the patient's congestive state.

It is also desirable that monitoring of patient vital signs occurs to ensure patient safety. Conventional patient monitors utilize one or more sensors with wires connecting the monitor to the patient.

SUMMARY

Patients in intensive care units (ICUs) or critical care units (CCUs) may require continuous monitoring of ECG and frequently other physiologic signals (such as invasive or non-invasive blood pressures, pulse oximetry, respiration, or $CO_2$ levels, among others). These signals are processed through their respective electronic signal channels in the patient monitor and may have differing amounts of time delay or latency as each signal undergoes different types of signal processing. Any differences in time delays among the signals are accounted for and corrected so the signals all align correctly once they are displayed on the patient monitor.

One approach to removing or reducing the stimulation artifacts is by adding additional filtering to the ECG signals prior to the ECG signals entering the patient monitor. This may be a viable approach in some circumstances, but any signal filtering applied external to the patient monitor will introduce some amount of time delay that results in the displayed ECG trace being misaligned with the other displayed physiologic signals. Small amounts of delay may be unnoticeable on the display, but larger delays will cause a noticeable ECG misalignment with respect to the other signals and potentially cause confusion or misinterpretation of a patient's condition. Typically, the more extensive or complex the filtering applied, the greater the resulting signal latency and the greater the onscreen misalignment of the ECG traces.

In some configurations, pre-filtering may include application of a notch filter or adaptive filter adapted to filter out 50 Hz and/or 60 Hz noise (e.g., typical 50 Hz and/or 60 Hz, 50 Hz-60 Hz, or other line frequency components) from the ECG signals or other biosignals. The pre-filtering may advantageously provide smoothing of the signals to which a denoising process (e.g., blanking and filtering) is to be applied.

If stimulation parameters such as frequency, amplitude, charge and recharge pulse widths, and waveform morphology are fixed, it may be possible to design filters with acceptable performance to satisfy both the artifact attenuation and latency requirements because these filters can be tailored to very specific signal characteristics. However, in an actual application these parameters are not always fixed, and the signal characteristics are not always predictable. For example, the stimulation artifact amplitude imposed on the ECG signal is not always predictable or even within known bounds. Most filters will either degrade or become ineffective if the ratio of artifact to ECG amplitude exceeds the capability of the filter. This is especially true if the artifact amplitude saturates the ECG signal channel, which may happen periodically.

ECG waveforms on patient monitors can be viewed and interpreted by qualified medical staff or automatically processed by algorithms in the patient monitors to identify, or detect, specific features or characteristics of the waveform. One basic extracted characteristic is heart rate. Others may be detection of certain cardiac arrhythmias that will automatically trigger alarms if they occur. For example, ventricular tachycardia or ventricular fibrillation can be deadly arrhythmias that require immediate intervention by the medical staff. They rely on the arrhythmia detection capability of the patient monitors to alert them to these conditions.

Patient monitors are used to provide feedback to clinicians regarding real-time patient health. The patient monitors are configured to display output relating to real-time physiological parameters or vital signs of the patient. Clinical professionals monitor the display output to determine the current status of the patient's health and to diagnose current patient conditions. In addition to visual display, the patient monitors may also be configured to generate audible output (e.g., alarms) if a particular physiological parameter or vital sign being monitored falls outside a threshold range to alert the clinical professionals of an unsafe condition that may require medical assistance or attention.

One example of a physiological parameter that is commonly monitored and displayed on patient monitors is heartbeat. The heartbeat may be displayed on a patient monitor as an electrocardiograph, or electrocardiogram, waveform (ECG or EKG) that is indicative of the electrical activity in the heart. The ECG waveform can be monitored by clinical professionals to determine whether any deviations or abnormalities occur that may be indicative of an unsafe and potentially life-threatening condition (e.g., atrial fibrillation, ventricular tachycardia, heart disease, cardiac arrest) that may require immediate medical attention or therapeutic treatment. The ECG waveform can be used to evaluate heart rate, rhythm, and other cardiac abnormalities and to make diagnoses.

Accordingly, it is desirable that the ECG waveform that is displayed on the patient monitor is clean and uncorrupted so as not to generate false alarms or prompt medical treatment that is not warranted and may cause harm to the patient. In addition, a clean ECG can ensure accurate diagnosis of patient conditions. The ECG waveform is obtained from multiple sensors (e.g., electrodes or leads) positioned on a skin of a patient at various locations on a patient's body (e.g., on chest, torso, neck, back, legs, and/or arms). The sensors transmit the heart's electrical activity to a ECG processing device or system. The ECG processing device or system generates a waveform or other output representative of the heart's electrical activity for display (e.g., on a patient monitor).

Unfortunately, the presence of electromagnetic energy generated from other electromagnetic energy sources in the vicinity of the ECG sensors can cause unwanted interference or noise to appear on the ECG waveform displayed on the patient monitor, especially if the frequency content of the ECG waveform, (e.g., electrical signals generated by the heart) and/or other interfering source overlap. This interference or noise can cause the clinical professionals, who are trained to be wary of any abnormalities on the ECG signal, to be alarmed and can render the ECG signals difficult or impossible to read, decipher or interpret. In addition, the interference or noise may cause automated "false" alarms or alerts to be generated because the interference or noise may cause the parameters being monitored to fall outside of a normal, expected condition or threshold range of values. The increase in false alarms may result in alarm fatigue.

One source of interference or noise on the ECG waveform can be a tissue modulation system configured to provide electrical modulation (e.g., electrical stimulation) to one or more nerves in and around a heart of a patient or to one or more nerves in and around vessels surrounding the heart (e.g., pulmonary arteries, pulmonary veins) to treat patients with acute decompensated heart failure. For example, catheters having stimulating elements (e.g., electrodes) may be temporarily inserted into or externally adjacent vessels surrounding the heart or into chambers of the heart to deliver electrical stimulation (e.g., electrical current or electrical pulses) to stimulate nerves (e.g., autonomic nerve fibers surrounding a pulmonary artery). These catheters may also cause interference or noise on the ECG waveform or signal when stimulation is being applied. In some implementations, implantable stimulators (e.g., pacemakers implanted in the heart), fluorescent lights in the vicinity of the patient, or other electromagnetic energy-emitting devices or structures (e.g., 50 Hz and/or 60 Hz line, 50 Hz-60 Hz, or other line frequency noise sources, magnetic resonance imaging machines, speakers) may be the source of interference on ECG waveforms when electrical stimulation (e.g., neurostimulation) is being applied.

In addition to being used in connection with neuromodulation (e.g., neurostimulation) systems for treatment of patients with acute decompensated heart failure, other applications can also benefit from several of the denoising techniques and systems described herein. For example, the denoising techniques and systems may be used in conjunction with systems adapted to perform any one or more of the following: spinal neuromodulation, pacing with a pacemaker, defibrillation with an implantable defibrillator or external defibrillation system, pulsed electrocautery, stimulation of nerves to treat urinary or fecal incontinence, muscle stimulation, prostate stimulation, brain and other neurological stimulation, stimulation of the vagus nerve, stimulation of osteoblasts, joint stimulation therapy to treat orthopedic conditions, iontophoresis, stimulation to determine tissue contact, electroanatomical mapping, other non-cardiac related functions, etc.

Methods of addressing the issue of electromagnetic energy (e.g., neurostimulator) device interference may vary depending on multiple factors. Most devices can be temporarily turned off in order to record short duration ECGs. Other procedures (such as imaging, electrophysiological, or ergometry) may require the devices to be inactivated for longer periods if this is tolerable for the patient. Some devices may be left operational if their stimulation artifacts (e.g., noise or interference on the ECG waveform caused by an electrical stimulation device or system) can be attenuated sufficiently by filtering within the front-end ECG instrument or system (e.g., low pass filters, band pass filters, notch filters, or other filters).

Several examples of the present disclosure provide for systems and methods of denoising (e.g., removing noise or interference from) a physiological parameter signal or waveform (e.g., biopotential, bio-signal, ECG, EKG) in real time (e.g., with minimal latency of less than 100 ms). The noise or interference may be caused for example, by application of electrical stimulation energy in the vicinity of the sensors (e.g., electrodes or leads) that are acquiring the physiological parameter signal (e.g., stimulation artifact). The denoising system may receive the signals from the ECG sensors. If electrical stimulation is not being applied, then the denoising system may be bypassed and not perform any denoising methods, algorithms or processes and the ECG waveform may be output for display (e.g., directly to a patient monitor or indirectly through telemetry units that transmit the ECG waveform to other display devices and/or central monitoring stations) as normal so as to advantageously affect (e.g., corrupt or impact) the ECG waveform as little as possible to improve fidelity. If electrical stimulation or other modulation is being applied (e.g., as determined by the denoising system from a signal or by automated processing algorithms or techniques), then the denoising system performs algorithms, methods, or techniques to remove the noise or interference caused by the electrical stimulation or other modulation (e.g., stimulation artifact) before the ECG waveform is output for display.

In some examples, the denoising system comprises, or alternatively consists essentially of, a filter subsystem or assembly configured to communicate with ECG leads configured to monitor a subject. The filter subsystem may comprise a digital signal processing system that is configured to produce a noise-filtered signal including the signals from the ECG leads minus noise from the neuromodulation system and send the noise-filtered signals to the patient monitor, or to a central monitoring system or other display via a telemetry unit (e.g., wirelessly). For example, the filter subsystem may include a filter adapted to remove 50 Hz and/or 60 Hz, 50 Hz-60 Hz, or other line frequency components from the ECG signal prior to and/or after other steps of a denoising process are performed in order to improve fidelity and accuracy of interpolation techniques performed during the denoising process. The denoising system may alternatively include one or more analog stages (e.g., unity gain amplifiers, sample-and-hold circuitry) to process ECG signals in an analog domain instead of a digital domain.

In some implementations, an apparatus for removing a transitory noise (e.g., temporary or transient noise) from a digitized biopotential (e.g., ECG waveform or signal) of a living being (e.g., human or animal) is provided. The transitory noise may be generated synchronous with electrical stimulation of a portion of a body (e.g. heart or vessels surrounding the heart, such as a pulmonary artery or vein) of the living being. The apparatus includes one or more processors configured to, upon execution of instructions stored on a non-transitory computer-readable medium, receive a synchronization signal (e.g., blanking pulse signal) from an electrical stimulation system (e.g., neurostimulator) indicative of timing of the electrical stimulation, remove the transitory noise from the digitized biopotential based upon the received synchronization signal, and interpolate across a gap created in the digitized biopotential to create a digitized biopotential free (or substantially free) of transitory noise. The transitory noise may only be removed during the synchronization signal (e.g., while the synchronization signal is indicative of electrical stimulation being applied to the portion of the body). In some implementations, the transitory noise is removed for a time corresponding to 0 to 5 (e.g., 1-5) milliseconds before until 0 to 5 (e.g., 1 to 5) milliseconds after receipt of the synchronization signal (e.g., due to time lag or delay). Interpolating across the gap may involve use of one or more of a linear, curvilinear, or cubic spline interpolation approach. Interpolation may include replacing removed data points or modifying existing data points with new values. For example, the interpolation may be based on known good values prior to and/or after the time period for which transitory noise is being removed from the digitized biopotential.

In accordance with several implementations, an apparatus for removing transitory noise from a biopotential (e.g., ECG waveform) of a living being is configured to receive a synchronization pulse from an electrical stimulation system indicative of timing of the electrical stimulation and remove said transitory noise from the biopotential based upon the received synchronization pulse using an analog-based approach. For example, a unity gain amplifier (or amplifier with other gain values) may be applied to the biopotential (e.g., ECG waveform) and a voltage level of the ECG waveform (or signal(s) thereof) may be sampled and held during the synchronization pulse (e.g., while the synchronization pulse is in a state indicative of stimulation being applied by the electrical stimulation system).

In accordance with several implementations, a denoising system is provided for denoising an ECG signal comprising transitory noise caused by application of electrical stimulation by an electrical stimulation device. The denoising system is (or is configured to be) communicatively coupled to an ECG electrode array (e.g., a plurality of ECG electrodes or sensors) configured to obtain ECG signals from a patient. The denoising system includes one or more processors (e.g., microcontrollers, signal processing circuitry) configured to, upon execution of stored instructions on a non-transitory computer-readable medium, detect portions of the ECG signal comprising the noise, and denoise the detected portions of the ECG signal comprising the noise. In this implementation, denoising the detected portions of the ECG signal includes blanking the detected portions of the ECG signal comprising the transitory noise (e.g., during a determined "blanking window") and modifying (e.g., reconstructing, interpolating) the blanked portions to produce a reconstructed ECG signal with reduced noise (e.g., free or substantially free of noise).

The one or more processors may be further configured to digitize the detected portions of the ECG signal comprising the noise. The one or more processors may be further configured to refine the reconstructed ECG signal using filtering in the digital or analog domain, such as a linear phase filter (e.g., a 40 Hz low pass filter, a band pass filter), a finite impulse response (FIR) filter, an infinite impulse response (IIR) filter, a Butterworth filter, and/or a Chebyshev filter to create a denoised ECG signal. In some implementations, the one or more processors are further configured to output the reconstructed ECG signal or the denoised ECG signal for display. In some implementations, the one or more processors are further configured to convert the denoised ECG signal into an analog signal to facilitate output on a display. The system may include a patient monitor comprising a display configured to display the output. The system may further include the ECG electrode array. The denoising system may comprise a fully integrated system comprising the electrical stimulation device, the patient monitor or other display, and/or the ECG front end system (e.g., ECG electrode array, leadwires, discrete electrical components and/or integrated chips) in addition to the components performing the denoising or may comprise a separate system configured to connect to the electrical stimulation device, patient monitor or display, and/or ECG front end system. In some implementations, the blanking step includes temporarily removing values stored at memory locations corresponding to the detected portions of the ECG signal comprising the noise and the modifying (e.g., reconstructing, interpolating) step includes calculating modified values to replace the removed values in the memory locations. For example, the modified values may be based, at least in part, on known good values obtained at memory locations of the ECG signal prior to and/or after the portion of the signal being blanked (e.g., before and/or after the blanking window). In some implementations, the blanking step includes decimating the detected portions of the ECG signal to remove data points (e.g., using down-sampling techniques) and then re-inserting data points during the modifying (e.g., reconstructing, interpolating) step.

In accordance with several implementations, a system for denoising an ECG signal comprising transitory noise caused by application of electrical stimulation by an electrical stimulation device includes one or more processors (e.g., microcontrollers, signal processing circuitry) configured to be communicatively coupled to an ECG electrode array (e.g., a plurality of ECG electrodes or sensors) configured to obtain ECG signals from a patient, the one or more processors configured to, upon execution of stored instructions on a non-transitory computer-readable medium, detect portions of a digitized ECG signal that comprise noise, and denoise the detected portions of the digitized ECG signal that comprise the noise. Denoising the detected portions of the digitized ECG signal can include blanking the detected portions of the ECG signal having the noise by temporarily removing values at memory locations corresponding to the detected portions of the ECG signal having the noise and replacing the removed values with modified values determined by modifying (e.g., reconstructing, interpolating) the detected portions of the digitized ECG signal comprising the noise to reconstruct the ECG signal as a denoised ECG signal with reduced noise (e.g., free or substantially free of transitory noise. The one or more processors are further configured to convert the denoised ECG signal to an analog signal using a digital-to-analog converter to facilitate display of the denoised ECG signal on a display.

The system may further include a patient monitor including the display. The system may also include the ECG electrode array and/or a front-end ECG monitoring system or hub. The one or more processors may optionally be further configured to refine the denoised ECG signal by applying further filtering to smooth out the denoised ECG signal (e.g., using a 50 Hz and/or 60 Hz or 50 Hz-60 Hz notch filter, a Butterworth notch filter or an adaptive noise cancellation filter to minimize signal latency that can be added by a more traditional linear time-invariant filter completely in series with the signal path) to remove 50 Hz, 60 Hz, 50 Hz-60 Hz, or other line frequency noise to smooth out ECG signals prior to and/or after blanking and/or modification (e.g., reconstruction, interpolation). The optional further filtering may be performed in the digital and/or analog domain and may include application of a linear phase filter (e.g., a low pass filter, a band pass filter, a notch filter), an FIR filter, an IIR filter, a Butterworth filter (e.g., Butterworth notch filter), and/or a Chebyshev filter. A digital FIR or IIR filter may be used that has a linear phase response but that is not a classical linear time-invariant analog filter. In some implementations, the ECG electrode array or front-end ECG monitoring system includes a band pass filter to refine the denoised ECG signal such that the separate optional further filtering is not required.

In accordance with several implementations, a method of denoising a physiological signal (e.g., a cardiac-related signal (e.g., an ECG signal, an intracardiac electrogram acquired from leads placed directly on or near the heart), a blood pressure signal) obtained from a patient that includes transitory (e.g., temporary or transient) noise caused by application of electromagnetic energy by a source of electromagnetic energy (e.g., an electrical stimulation system or device) located within or adjacent the patient is provided. For example, the source may be a neurostimulator positioned within a vessel (e.g., pulmonary artery or vein) surrounding a heart or within a chamber of a heart. The method includes detecting portions of the physiological signal comprising the transitory noise, blanking the detected portions of the physiological signal comprising the transitory noise, and modifying (e.g., reconstructing, interpolating) the detected portions of the physiological signal comprising the transitory noise to reconstruct the physiological signal as a reconstructed physiological signal. The detecting, blanking and modifying (e.g., reconstructing, interpolating) may be performed by one or more processors (e.g., microcontrollers, signal processing circuitry) executing instructions stored on a non-transitory computer-readable medium. The blanking and modifying (e.g., reconstructing, interpolating) may be performed using a digital-based or analog-based approach. The blanking may include temporarily removing values at memory locations corresponding to the detected portions of the physiological signal having the transitory noise and the modifying (e.g., reconstructing, interpolating) may include replacing the removed values during the blanking window with modified values. For example, the modified values may be based, at least in part, on known good values of the physiological signal corresponding to times prior to and/or after the blanking window during which blanking is performed. In accordance with at least several embodiments, the method of denoising may not involve applying wavelet transforms (e.g., discrete wavelet transforms, quadratic spline wavelets) and may not filter out only asynchronous noise.

In some implementations, the step of detecting portions of the physiological signal that comprise the transitory noise is based on a synchronization pulse (e.g., blanking pulse) received from an electrical tissue modulation system that is likely to generate the transitory noise on the physiological signal. The blanking pulse may be received prior to initiation of electrical neuromodulation therapy by the electrical tissue modulation system or generally coincident with initiation of electrical neuromodulation therapy by the electrical neuromodulation system. In some implementations, the blanking pulse is continuously in a state (e.g., "on" state) indicative of therapy being applied for an entire duration of the electrical neuromodulation therapy. The method may also include digitizing the portions of the physiological signal having the transitory noise using an analog-to-digital converter prior to blanking the detected portions of the physiological signal having the transitory noise. The method may also include converting the denoised physiological signal into an analog signal using a digital-to-analog converter to facilitate output of the denoised physiological signal on a display. In other implementations, the portions of the physiological signal are not digitized and the blanking is performed using an analog-based approach by passing the signal through a unity gain amplifier (or amplifier with other gain values) and then sampling and holding the voltage at a constant level while the blanking pulse is in a state indicative of therapy being applied. The analog denoised signal may be output to the display. The display may be a display on a patient monitor or a central monitoring system of a clinical facility.

In some implementations, the method further includes determining whether a physiological parameter of the physiological signal falls outside of a threshold range and generating an alert if the physiological parameter of the physiological signal falls outside of the threshold range. The method may also optionally include refining the reconstructed physiological signal to smooth out the reconstructed physiological signal to create a denoised physiological signal without the transitory noise. In various implementations, a quality of signal reconstruction (as defined, for example, by the QSR equation provided herein) of the denoised physiological signal is greater than 95% (e.g., greater than 96%, greater than 97%, greater than 98%, about 99%).

In accordance with several implementations, a method of denoising an ECG signal comprising transitory noise caused by application of electrical stimulation by an electrical stimulation device includes detecting portions of the ECG signal comprising the transitory noise, removing values at memory locations corresponding to the detected portions of the ECG signal comprising the transitory noise, and replacing the removed values with modified values by modifying (e.g., reconstructing, interpolating) the detected portions of the ECG signal comprising the transitory noise to reconstruct the ECG signal as a reconstructed ECG signal. The detecting, removing, and modifying (e.g., reconstructing, interpolating) steps may be performed by one or more processors (e.g., microcontrollers, signal processing circuitry) executing instructions stored on a non-transitory computer-readable medium.

The method may further optionally include refining the reconstructed ECG signal with a filter to smooth out the reconstructed ECG signal to create a denoised ECG signal, wherein the filter is a linear phase filter, a Butterworth filter, an FIR filter, an IIR filter, and/or a Chebyshev filter. In some implementations, the method includes amplifying the ECG signal before removing values at memory locations corresponding to the detected portions of the ECG signal. The method may also include obtaining the ECG signal from a subject using at least two ECG leadwires (e.g., single lead/channel having two leadwires, two-channel ECG input having two vectors, single channel ECG with a single lead, 3 electrodes and 3 leadwires). The step of detecting the portions of the ECG signal including the transitory noise may advantageously be based on a blanking pulse signal received from the electrical stimulation device in some implementations. The method may include digitizing the portions of the ECG signal having the transitory noise (e.g., portions of the ECG signal during a determined blanking window) using an analog-to-digital converter prior to removing values at memory locations corresponding to the detected portions of the ECG signal having the transitory noise. The method may further include converting the denoised ECG signal into an analog signal using a digital-to-analog converter to facilitate output of the denoised ECG signal on a display. The method may also include outputting the analog signal to the display, which could be on a patient monitor or a central monitoring system.

In some implementations, the method includes determining whether a physiological parameter of the ECG signal falls outside of a threshold range or is indicative of an abnormal heart rhythm. The method may include generating an alert if the physiological parameter of the ECG signal falls outside of the threshold range or is indicative of an abnormal heart rhythm, wherein the alert is at least one of an audible alert and a visual alert. The alert may be configured to terminate electrical stimulation being provided by the electrical stimulation device.

In accordance with several implementations, a method of denoising an ECG waveform obtained from a patient, wherein the ECG waveform comprises transitory noise caused by application of electrical stimulation by an electrical stimulation system located within or adjacent the patient, includes receiving a synchronization pulse from the electrical stimulation system indicative of initiation of stimulation by the electrical stimulation system and removing the transitory noise from the ECG waveform based upon the received synchronization pulse using an analog-based approach. The analog-based approach may include applying a unity gain amplifier (or amplifier with other gain values) to an input analog ECG signal, sampling a voltage level of the input analog ECG signal at a first time instance corresponding to the received synchronization pulse, and holding at the voltage level until the synchronization pulse transitions to a state indicative of termination of stimulation by the electrical stimulation system. The terms "synchronization pulse" and "blanking pulse" may be used interchangeably herein.

In accordance with several implementations, a system for denoising physiological signals indicative of a patient parameter is configured to determine whether a physiological signal (or at least portions of the physiological signal) received by the one or more processors comprises transitory noise. If it is determined that the physiological signal comprises transitory noise, the system is configured to denoise the physiological signal (or at least the portions of the physiological signal determined to comprise transitory noise). Denoising the physiological signal may include removing values in memory locations corresponding to portions of the physiological signal having the transitory noise and modifying (e.g., reconstructing, interpolating) the portions of the physiological signal having the transitory noise to replace the removed values with modified values based on said modifying (e.g., reconstructing, interpolating) to reconstruct the physiological signal as a denoised physiological signal. If it is determined that the physiological signal (or at least portions of the physiological signal) does not comprise transitory noise caused by application of electrical stimulation by an electrical stimulation device, the denoising system is configured to cause the physiological signal (or those portions of the physiological signal determined not to comprise transitory noise) to be output for display without modifying the physiological signal. The system may include one or more processors (e.g., microcontrollers, digital signal processing circuitry) configured to, upon execution of stored instructions on a non-transitory computer-readable medium, perform the recited steps. In some implementations, some of the steps may alternatively be performed using analog circuitry or stages (e.g., unity gain amplifiers and sample-and-hold circuitry).

The physiological signal may include at least one of: a cardiac-related signal such as an ECG signal or intracardiac electrograms acquired from leads placed directly on the heart, a blood pressure signal, and a respiratory rate signal. The denoised physiological signal may have a quality of signal reconstruction of greater than 95% (e.g., greater than 95%, greater than 96%, greater than 97%, greater than 98%, about 99%). The denoising system may be configured to make the determination of whether the physiological signal comprises the transitory noise based on a received blanking pulse signal indicative of application of electrical stimulation by the electrical stimulation device. The blanking pulse signal may be generated by the electrical stimulation device and transmitted to the system (e.g., one or more processors of the system) through a physical electrical connection or through a wireless connection. In some implementations, the denoising system is configured to make the determination of whether the physiological signal comprises the noise based on characteristics of the physiological signal (e.g., ECG signal). The modifying (e.g., reconstructing, interpolating) may include use of one or more of: linear, curvilinear, and cubic spline interpolation. The system may further include an analog-to-digital converter configured to digitize the physiological signal and a digital-to-analog converter configured to convert the denoised physiological signal into an analog signal. The system may optionally include a linear phase filter configured to smooth out the reconstructed physiological signal after interpolation. Other non-linear phase filters may alternatively be used. The system may also include a patient monitor comprising a display configured to display the denoised ECG signal. The system may optionally include an alert generation subsystem configured to generate an alarm event if a characteristic of the physiological signal is outside of a threshold range.

In accordance with several embodiments, a system for denoising an ECG waveform includes an ECG electrode array configured to obtain ECG signals from a patient and one or more processors configured to be communicatively coupled to the ECG electrode array. The one or more processors are configured to, upon execution of stored instructions on a non-transitory computer-readable medium, determine whether an ECG signal received from the ECG electrode array comprises transitory noise caused by application of electrical stimulation by an electrical stimulation device. If it is determined that the ECG signal comprises transitory noise caused by application of electrical stimulation by an electrical stimulation device, the one or more processors are configured to digitize the ECG signal using an analog-to-digital converter and denoise the digitized ECG signal. Denoising the digitized ECG signal may include removing values in memory locations corresponding to portions of the digitized ECG signal having the transitory noise and modifying (e.g., reconstructing, interpolating) the portions of the digitized ECG signal having the transitory noise to replace the removed values with modified values based on said interpolating to reconstruct the ECG signal as a reconstructed ECG signal. The one or more processors are further configured to refine the reconstructed ECG signal using a linear phase filter (e.g., a low pass filter, a band pass filter, and a notch filter) to create a denoised ECG signal, convert the denoised ECG signal to an analog signal using a digital-to-analog converter, and output the denoised ECG signal for display on a patient monitor. If it is determined that the ECG signal does not comprise transitory noise caused by application of electrical stimulation by the electrical stimulation device, the one or more processors are configured to cause the ECG signal to be output for display on the patient monitor without modifying the ECG signal. Non-linear phase filters (e.g., a Butterworth filter, and/or a Chebyshev filter) may also be used to refine the reconstructed ECG signal.

The denoising system may include a stimulation detection subsystem configured to make the determination of whether the ECG signal comprises the transitory noise caused by application of electrical stimulation by the electrical stimulation device. The stimulation detection subsystem may be configured to make the determination based on a received blanking pulse signal indicative of application of electrical stimulation by the electrical stimulation device. The blanking pulse signal may be generated by the electrical stimulation device and transmitted to the denoising system through a physical electrical connection or a wireless connection. The stimulation detection subsystem may be configured to make the determination based on characteristics of the ECG signal (e.g., an R-R interval between successive R waves of the ECG signal). The system may include the patient monitor comprising a display. The system can optionally include an alert generation subsystem configured to generate an alert if a characteristic of the ECG signal is out of a threshold range. In some implementations, the denoising system includes one or more switches configured to open and close based on the determination of whether the ECG signal received from the ECG electrode array comprises transitory noise.

In accordance with several implementations, a therapeutic system includes an electrical stimulation system configured to apply electrical stimulation to a nerve within or surrounding a vessel adjacent a heart of a patient. The therapeutic system further includes a denoising system configured to remove noise artifact caused by the electrical stimulation system from an ECG signal received by one or more ECG leads (e.g., electrodes and leadwires) coupled to the patient by blanking, modifying (e.g., reconstructing, interpolating), and optionally refining the ECG signal to construct a denoised ECG signal. The blanking and/or interpolating may be performed digitally by one or more processors or using analog circuitry. The therapeutic system also includes a physiological parameter determination subsystem, the physiological parameter determination subsystem including one or more processors configured to, upon execution of stored instructions on a non-transitory computer-readable medium determine whether a physiological parameter being monitored is outside of a threshold range based, at least in part, on signals indicative of the physiological parameter received from one or more sensors coupled to or positioned within the patient. When the physiological parameter determination subsystem determines that the physiological parameter is outside of the threshold range, application of electrical stimulation by the electrical stimulation system is terminated and the denoising system is bypassed. When the physiological parameter determination subsystem determines that the physiological parameter is within the threshold range, application of electrical stimulation by the electrical stimulation system continues and the ECG signal is processed by the denoising system. The one or more sensors coupled to or positioned within the patient may include one or more pressure sensors positioned within a chamber of the heart and/or within a pulmonary artery. The physiological parameter may be heart rate.

In some implementations, when the physiological parameter determination subsystem determines that the physiological parameter is outside of the threshold range, the physiological parameter determination subsystem generates a stimulation termination signal to be sent to the electrical stimulation system and/or an alert. The alert may be audible and/or visible (e.g., output on a display of a patient monitor. The alert may additionally or alternatively be transmitted to a central monitoring station of a patient care facility. In some implementations, the alert is transmitted to a mobile communications device of one or more clinical professionals over a communication network (e.g., wireless network, telecommunications network, paging network, cellular network).

Several embodiments of the invention are particularly advantageous because they include one, several or all of the following benefits: (i) removal of unwanted or undesired noise artifact or interference from biological or physiological parameter signals; (ii) reduced processing or computing times; (iii) deterministic algorithms as opposed to predictive or reactive algorithms; (iv) preservation of fidelity and morphology of original waveforms; (v) reduction in false alarms or alarm fatigue; (vi) ensured accuracy of patient diagnoses; (vii) increased patient safety; (viii) ability to provide continuous treatment and monitoring for several days; (ix) improved "real-time" behavior (especially in memory) of digital signal processing systems vs. other digital techniques given the lag time requirements, and/or (x) simpler solutions due to synchronization.

The methods summarized above and set forth in further detail below describe certain actions taken by a practitioner; however, it should be understood that they can also include the instruction of those actions by another party. Thus, actions such as "positioning an electrode" include "instructing positioning of an electrode."

For purposes of summarizing the invention and the advantages that may be achieved, certain objects and advantages are described herein. Not necessarily all such objects or advantages need to be achieved in accordance with any particular example. In some examples, the invention may be embodied or carried out in a manner that can achieve or optimize one advantage or a group of advantages without necessarily achieving other objects or advantages.

The examples disclosed herein are intended to be within the scope of the embodiments herein disclosed. These and other examples will be apparent from the following detailed description having reference to the attached figures, the embodiments not being limited to any particular disclosed example(s). Optional and/or preferred features described with reference to some examples may be combined with and incorporated into other examples.

BRIEF DESCRIPTION OF THE DRAWINGS

FIG. 8A schematically illustrates an example ECG waveform uncorrupted by application of neurostimulation.

FIG. 8B schematically illustrates an example ECG waveform that is corrupted by application of stimulation to a portion of a body of a living subject.

FIGS. 9A and 9B illustrate close-up exploded views of portions of the corresponding ECG waveforms of FIGS. 8A and 8B, respectively.

FIGS. 11A and 11B illustrate an ECG waveform indicative of bigeminy during application of neurostimulation without denoising and with denoising, respectively.

DETAILED DESCRIPTION

Figure 1:
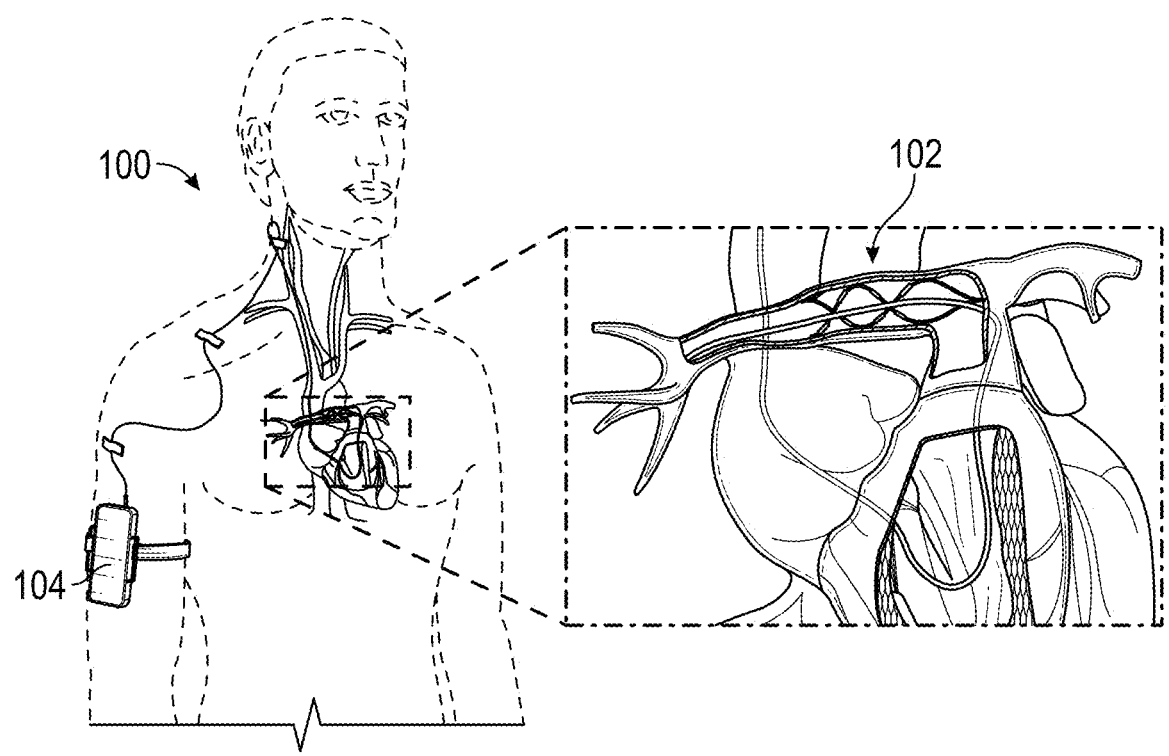
FIG. 1 schematically illustrates a system that can be used to apply electrical stimulation to one or more nerves in and around the heart of a subject.

Patient monitors are used to provide feedback to clinicians in hospitals, nursing homes and other patient care facilities regarding real-time patient health. The patient monitoring devices are configured to display output relating to real-time physiological parameters or vital signs of the patient. Clinical professionals monitor the display output to determine the current status of the patient's health and possibly increase the level of medical care given to the patient based on the current status. The clinical professionals may diagnose patient conditions or illnesses or prescribe treatments based on the monitored physiological parameters, biopotentials, or vital signs. In addition to visual display of textual, numerical, or graphical information or data corresponding to the physiological parameters, biopotentials, or vital signs, the patient monitors may also be configured to generate visual or audible output (e.g., alerts or alarm events) if a particular physiological parameter, biopotential, or vital sign being monitored falls outside a threshold range (e.g., safety limits) to alert the clinical professionals of an unsafe condition that may require medical assistance or attention. Accordingly, it can be advantageous to make sure that the physiological parameters (or the output indicative of the physiological parameters) that are displayed and monitored by the patient monitors are accurate and reliable to reduce alarm fatigue and ensure accurate diagnosis.

Physiological parameters can include heart rate, blood pressure, temperature, or the like. One example of a physiological parameter that is commonly monitored and displayed on patient monitors is heartbeat. The heartbeat may be displayed on a patient monitor as an electrocardiograph, or electrocardiogram, waveform (ECG or EKG) that is indicative of the electrical activity in the heart. The ECG waveform can be monitored by clinical professionals to determine whether any deviations or abnormalities occur that may be indicative of an unsafe and potentially life-threatening condition (e.g., atrial fibrillation, ventricular tachycardia, heart disease, cardiac arrest) that may require immediate medical attention or therapeutic treatment. The ECG waveform can be used to evaluate heart rate, rhythm, and other cardiac abnormalities and to make diagnoses.

Accordingly, it is desirable that the ECG waveform that is displayed on the patient monitor is clean and uncorrupted so as not to generate false alarms or prompt medical treatment that is not warranted and may cause harm to the patient. In addition, ECG waveforms corrupted with noise may cause a practitioner to miss an abnormal event or occurrence (e.g., arrhythmia) and withhold therapy that should not have been withheld. The ECG waveform is derived from signals or measurements from multiple sensors (e.g., electrodes and/or leads or leadwires) positioned on a skin of a patient at various locations on a patient's body. The sensors transmit the heart's electrical activity to an ECG processing device or system. The ECG processing device or system generates a waveform or other output representative of the heart's beats and electrical activity for display (e.g., on a display of a patient monitor).

Unfortunately, the presence of electromagnetic energy generated from other electromagnetic energy sources in the vicinity of the ECG sensors can cause unwanted interference or noise to appear on the ECG waveform displayed on the patient monitor, especially if the frequency content of the ECG waveform (e.g., electrical signals generated by the heart) and the other interfering source overlap. This interference or noise can cause the clinical professionals, who are trained to be wary of any abnormalities on the ECG signal, to be alarmed and can render the ECG signals difficult or impossible to read, decipher, or interpret. In addition, the interference or noise may cause automated "false" arrhythmia alarms or alerts to be generated because the interference or noise may cause the parameters being monitored to fall outside of a normal, expected condition or threshold range (e.g., safety limits). The increase in false alarms may result in alarm fatigue.

One source of temporary, transient, or transitory, interference or noise can include a tissue modulation system configured to provide electrical modulation (e.g., electrical stimulation, electrical ablation, electrical denervation) to one or more nerves in and around a heart of a patient or to one or more nerves in and around vessels surrounding the heart (e.g., pulmonary arteries, pulmonary veins) to treat patients with acute decompensated heart failure. Catheters having stimulating elements (e.g., stimulatory electrodes) may be temporarily inserted into, or positioned externally adjacent, vessels surrounding the heart or chambers of the heart to deliver electrical stimulation (e.g., electrical current or electrical pulses) to stimulate nerves (e.g., autonomic nerve fibers surrounding a pulmonary artery). These catheters may also cause interference or noise (e.g., stimulation artifact) to appear on the ECG waveform when stimulation is being applied by the stimulating elements of the catheters.

The degree of interference varies depending on the location of the stimulation electrodes and the characteristics of the stimulation waveform. As another example, pacemakers or other implantable stimulators implanted near the heart may cause interference (e.g., stimulation artifact) on a display of the ECG waveform when stimulation (e.g., electrical current or electrical pulses) is being applied.

In addition to being used in connection with neuromodulation (e.g., neurostimulation) systems for treatment of patients with acute decompensated heart failure, other applications can also benefit from several of the denoising techniques and systems described herein. For example, the denoising techniques and systems described herein may be used in conjunction with systems adapted to perform any one or more of the following: spinal neuromodulation, pacing with a pacemaker, defibrillation with an implantable defibrillator or external defibrillation system, pulsed electrocautery, stimulation of nerves to treat urinary or fecal incontinence, muscle stimulation, prostate stimulation, brain or other central or peripheral neurological stimulation, stimulation of the vagus nerve, stimulation of osteoblasts, joint stimulation therapy to treat orthopedic conditions, iontophoresis, stimulation to determine tissue contact, imaging, electroanatomical mapping or electrophysiology recordings, ergometry, etc.

FIG. 1 schematically illustrates an example tissue modulation system 100 that can be used to apply electrical modulation to tissue (e.g., including one or more nerves) in and around the heart of a subject that may generate interference or noise on an ECG waveform while the electrical modulation is being applied. In one implementation, the tissue modulation system 100 comprises a cardio pulmonary nerve stimulation (CPNS) system that is intended to treat patients in acute decompensated heart failure. The CPNS system can cause electrical interference (e.g., stimulation artifact) to appear on biopotentials, such as ECG waveforms on a display that is being monitored by a clinician or practitioner).

In some implementations, the location of the electrodes of the CPNS system are intended to be near the heart, which is also the source of the ECG signals, and the stimulation waveform of the CPNS system has frequency components that overlap that of the ECG signals. Accordingly, the presence of the stimulation artifact on the ECG signals caused by the CPNS system makes the ECG waveform difficult to accurately interpret by trained practitioners and renders automatic arrhythmia detection functions on ECG patient monitors ineffective.

The tissue modulation system 100 may be configured to deliver nerve stimulation as either continuous or intermittent biphasic pulse trains through a catheter placed temporarily in the upper thorax near the heart. Patients receiving therapy are typically treated in intensive care units (ICUs) or cardiac care units (CCUs) within hospitals and are kept on continuous surface electrocardiogram (ECG) monitoring for up to five days.

In accordance with several implementations, dealing with CPNS-generated interference is more challenging than with other neurostimulator devices for several reasons: (1) the neurostimulator provides therapy, and as such, can't be turned off during patient monitoring, (2) the neurostimulation therapy can be delivered for a long continuous duration of time (e.g., up to five days), while requiring patient monitoring the entire time, (3) the CPNS electrodes can be directly in line with the ECG vectors, causing a large amplitude interference artifact, and/or (4) the interference frequency spectrum typically overlaps the ECG frequency spectrum, thereby precluding the use of ECG instrument filters.

The system 100 comprises a first component 102 and a second component 104. The first component 102 may be positioned in a pulmonary artery (e.g., the right pulmonary artery as shown in FIG. 1, the left pulmonary artery, and/or the pulmonary trunk). The first component 102 may be endovascularly positioned via a minimally invasive, transdermal, percutaneous procedure, for example routed through the vasculature from a remote location such as a jugular vein (e.g., an internal jugular vein, as shown in FIG. 1), an axial subclavian vein, a femoral vein, or other blood vessels. Such an approach can be over-the-wire, using a Swan-Ganz float catheter, combinations thereof, etc. In some examples, the first component may be positioned invasively, for example during conventional surgery (e.g., open-heart surgery), placement of another device (e.g., coronary bypass, pacemaker, defibrillator, etc.), or as a stand-alone procedure. As described in further detail herein, the first component comprises a neuromodulator (e.g., electrode, transducer, drug, ablation device, ultrasound, microwave, laser, cryotherapy, combinations thereof, and the like) and may optionally comprise a stent or framework, an anchoring system, and/or other components. The first component 102 may be acutely positioned in the pulmonary artery for 24 to 120 hours. In some examples, the first component 102 neuromodulates terminal branches within the cardiac plexus, which can increase left and/or right ventricle contractility and/or relaxation. The increase in ventricular cardiac output due to the contractility increase may occur without a corresponding increase in heart rate, or may be greater than (e.g., based on a percentage change) that due to an increase in heart rate alone. In some examples, the first component 102 may be adapted to ablate tissue, including nerves, in addition to or instead of stimulating tissue, such as nerves.

The first component 102 is electrically coupled to the second component 104 (e.g., via wires or conductive elements routed via a catheter, for example as illustrated in FIG. 1, and/or wirelessly). The second component 104 may be positioned extracorporeally (e.g., strapped to a subject's arm as shown in FIG. 1, strapped to another part of the subject (e.g., leg, neck, chest), placed on a bedside stand, etc.). In some examples, the second component 104 may be temporarily implanted in the subject (e.g., in a blood vessel, in another body cavity, in a chest, etc.). The second component 104 includes electronics (e.g., pulse generator) configured to operate the electrode in the first component 102. The second component 104 may include a power supply or may receive power from an external source (e.g., a wall plug, a separate battery, etc.). The second component 104 may include electronics configured to receive sensor data.

The system 100 may comprise one or more sensors (e.g., pressure sensor). The sensor(s) may be positioned in one or more of a pulmonary artery (e.g., right pulmonary artery, left pulmonary artery, and/or pulmonary trunk), an atrium (e.g., right and/or left), a ventricle (e.g., right and/or left), a vena cava (e.g., superior vena cava and/or inferior vena cava), and/or other cardiovascular locations. The sensor(s) may be part of the first component 102, part of a catheter, and/or separate from the first component 102 (e.g., electrocardiogram chest monitor, pulse oximeter, etc.). The sensor(s) may be in communication with the second component 104 (e.g., wired and/or wireless). The second component 104 may initiate, adjust, calibrate, cease, etc. neuromodulation based on information from the sensor(s). Measurements obtained from the sensor(s) (e.g., pressure sensors) may be used to determine whether a patient condition is within a "safe" or acceptable range within which stimulation (and denoising processes) may be applied. Otherwise, stimulation may be halted and the denoising systems may be bypassed to increase patient safety and reduce processing times and complexity.

The system 100 may comprise an "all-in-one" system in which the first component 102 is integral or monolithic with the targeting catheter. For example, the first component 102 may be part of a catheter that is inserted into an internal jugular vein, an axial subclavian vein, a femoral vein, etc. and navigated to a target location such as the pulmonary artery. The first component 102 may then be deployed from the catheter.

The system 100 may comprise a telescoping and/or over-the-wire system in which the first component 102 is different than the targeting catheter. For example, a targeting catheter (e.g., a Swan-Ganz catheter) may be inserted into an internal jugular vein, an axial subclavian vein, a femoral vein, etc. and navigated to a target location such as the pulmonary artery (e.g., by floating). A guidewire may be inserted into a proximal hub through the target catheter to the target location (e.g., having a stiffest portion exiting the target catheter distal end) and the first component 102 as part of a separate catheter than the target catheter may be tracked to the target location over the guidewire or using telescoping systems such as other guidewires, guide catheters, etc. The first component 102 may then be deployed from the separate catheter. Such systems are known by interventional cardiologists such that multiple exchanges may be of little issue. Such a system may allow customization of certain specific functions. Such a system may reduce overall catheter diameters, which can increase trackability, and/or allow additional features to be added, for example because not all functions are integrated into one catheter. Such a system may allow use of multiple catheters (e.g., removing a first separate catheter and positioning a second separate catheter without having to reposition the entire system). For example, catheters with different types of sensors may be positioned and removed as desired. The system 100 may be steerable (e.g., comprising a steerable catheter) without a Swan-Ganz tip. Some systems 100 may be compatible with one or more of the described types of systems (e.g., a steerable catheter with an optionally inflatable balloon for Swan-Ganz float, a steerable catheter that can be telescoped over a guidewire and/or through a catheter, etc.).

Figure 2:
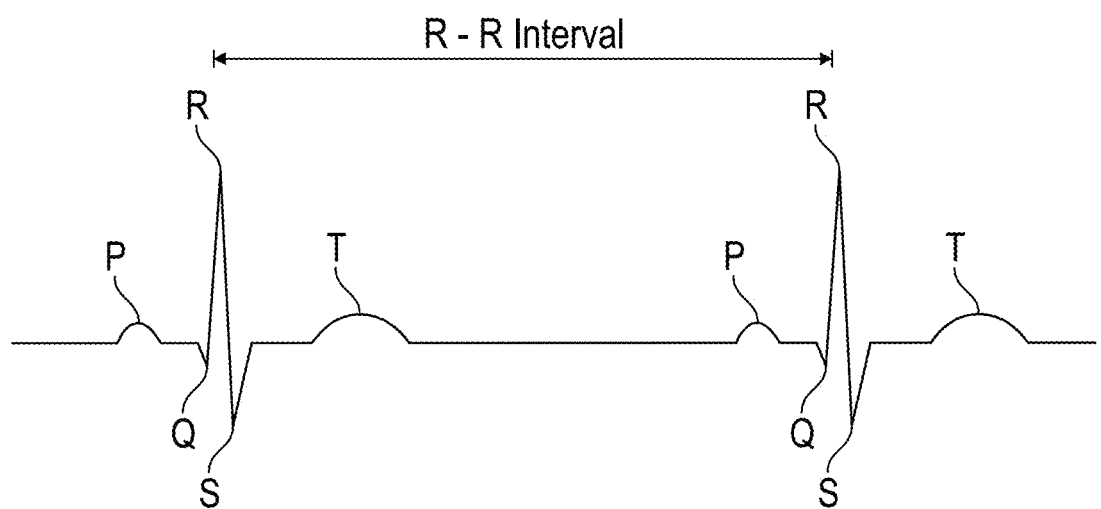
FIG. 2 schematically illustrates an example electrocardiograph.

FIG. 2 schematically illustrates a portion of an example electrocardiograph, or electrocardiogram, (ECG or EKG) waveform. The ECG waveform includes P waves, Q waves, R waves, S waves, and T waves, which are each indicative of different events during a single heartbeat of a healthy subject (e.g., patient). The P wave represents atrial depolarization, which causes the left atrium and the right atrium to push blood into the left ventricle and right ventricle, respectively. The flat period until the Q wave, the "PR Segment," and the start of the P wave to the start of the Q wave is the "PR Interval." The Q wave, the R wave, and the S wave, together the "QRS Complex," represent ventricular depolarization, which causes the right ventricle to push blood into the pulmonary artery and towards the lungs and which causes the left ventricle to push blood into the aorta for distribution to the body. The T wave represents repolarization of the left and right ventricles. The flat period until the T wave is the "ST Segment" during which the ventricles are depolarized, and collectively the QRS Complex, the ST Segment, and the T wave are the "QT Interval." The duration between successive R waves or peaks is the "R-R interval."

Some ECGs also have a U wave after the T wave. The timing, amplitude, relative amplitude, etc. of the various waves, segments, intervals, and complexes can be used to diagnose various conditions of the heart.

Figure 3A:
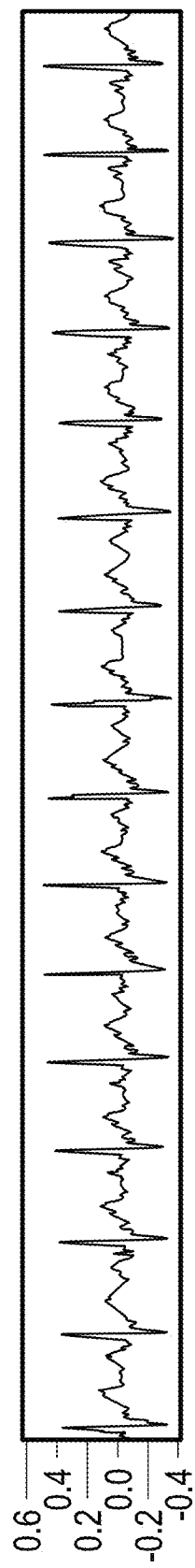
FIG. 3A illustrates an example of an ECG signal when no electrical stimulation is being applied by a stimulation system.
Figure 3B:
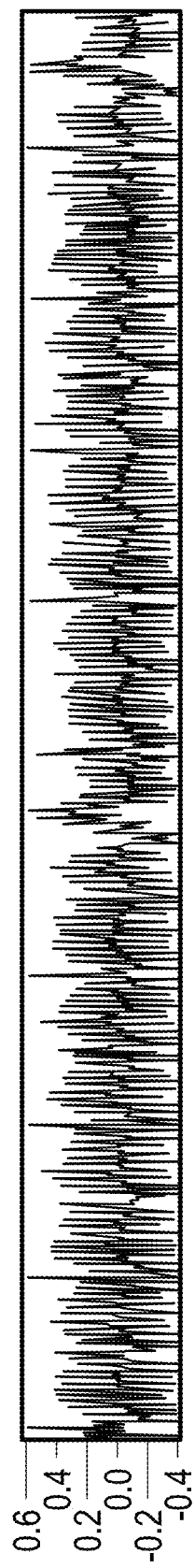
FIG. 3B illustrates an example of an ECG signal when electrical stimulation is being applied by a stimulation system.

Electrical modulation (e.g., stimulation) from a tissue modulation system (such as the systems described herein) or from other electromagnetic energy generating systems or devices (e.g., radiofrequency energy delivery systems, ultrasound energy delivery systems, microwave energy delivery systems, laser devices, implantable stimulators, transcutaneous electrical stimulation devices, pacemakers, defibrillators, imaging devices, lighting equipment, electrophysiology recording or mapping devices) located in a region near one or more of the ECG leads or leadwires may interfere with (e.g., cause distortion of, or noise to appear on) a display of a "clean" true ECG waveform. FIG. 3A illustrates an example portion of a clean ECG waveform when no electrical stimulation is being applied by a stimulation system, such that no interference or noise (e.g., stimulation artifact) is present on the displayed waveform. FIG. 3B illustrates an example portion of the ECG waveform when electrical stimulation is being applied by a stimulation system. As can be seen in FIG. 3B, the interference or noise created by the stimulation source makes it difficult to distinguish the normal ECG waveform (e.g., the features indicative of the heart beats) and the noise or interference (e.g., stimulation artifact). In some examples, the portion of the ECG waveform may be modified to account for (e.g., remove, filter out, suppress, cancel out) such interference or noise (e.g., stimulation artifact) and display a true, or accurate, portion of the ECG waveform (e.g., high-fidelity waveform without compromising original morphology) even while electrical modulation (e.g., electrical stimulation) is being applied to the patient (e.g., by a neuro stimulation system).

The ECG waveform (e.g., one or more portions of the ECG waveform) could be artificially flat-lined or ignored during periods of stimulation and the clinical professionals could rely on alternative physiological parameters or vital signs to ensure patient safety during periods of stimulation. However, many clinical professionals may not be comfortable with periods of time in which the true ECG waveform is not being accurately displayed. In addition, as mentioned previously, the periods of artificial flat-lining or "blanking" may cause false alarms to be generated, causing unnecessary worry or stress to the patient or clinicians, or even prompting spontaneous, unwarranted medical action that results in harm, or even death, to the patient. Accordingly, several implementations described herein denoise the ECG waveform by modifying or replacing ECG waveform values at certain time instances instead of zeroing the values out or removing the values at those time instances without replacing them with alternative values. Accordingly, the data sets before and after denoising may be the same size.

Figure 4:
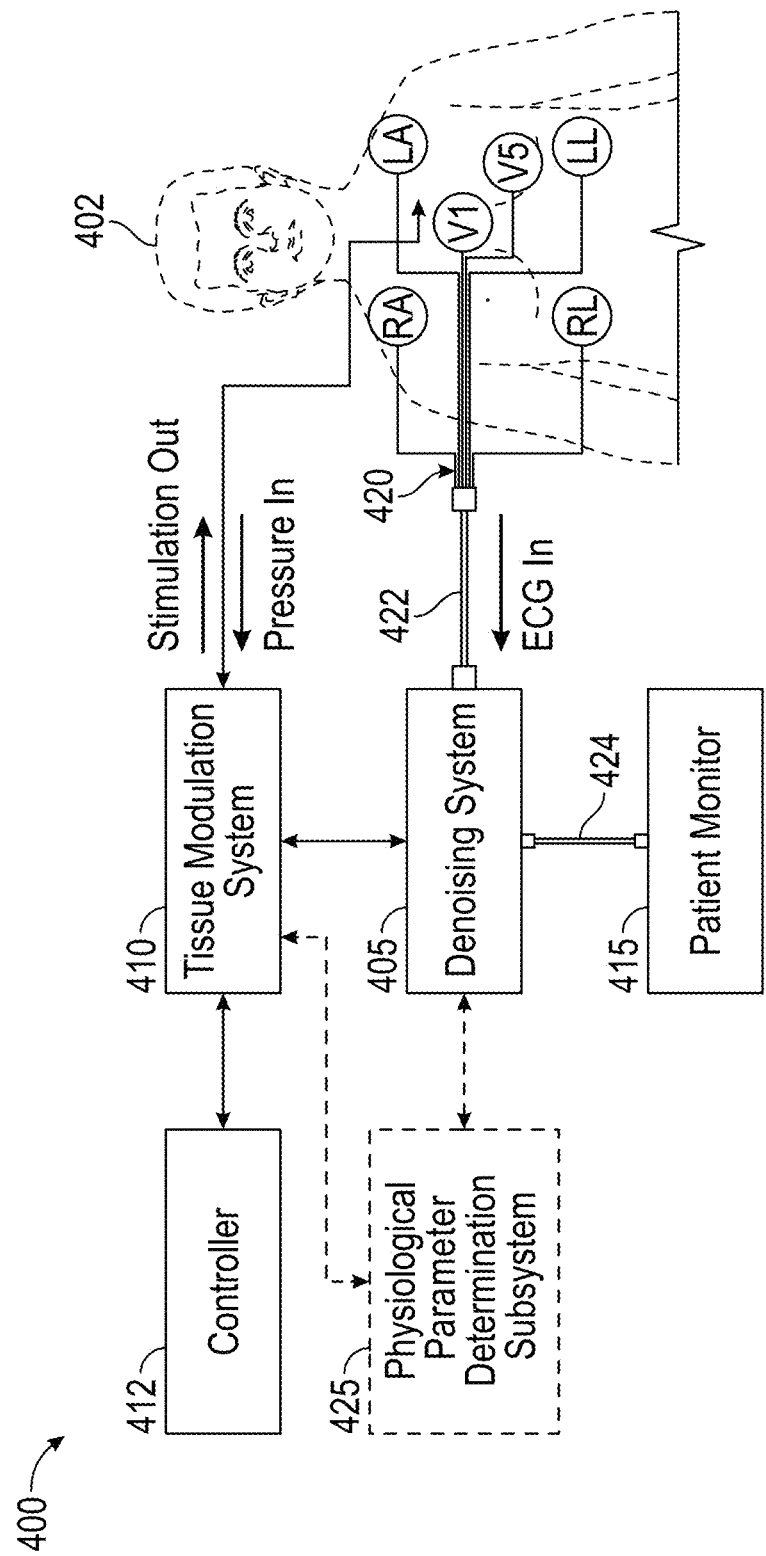
FIG. 4 schematically illustrates an example of a denoising system.

FIG. 4 schematically illustrates an example treatment and patient monitoring system 400 that includes a denoising system 405 configured to advantageously remove (e.g., filter out) the unwanted noise or interference (e.g., stimulation artifact) generated by a stimulation system 410 while preserving the fidelity and morphology of the ECG waveform that is displayed on a patient monitor or other display device 415. The treatment and patient monitoring system 400 includes a controller or control unit 412 configured to control therapy delivery by the stimulation system 410 to a living subject (e.g., patient) 402. The controller or control unit 412 may comprise a computing device (e.g., computer, laptop, tablet, smartphone) that includes one or more processing devices (e.g., microcontrollers) and circuitry configured to execute one or more stored programs or algorithms (e.g., to generate electrical stimulation pulses of desired patterns and durations). The control unit 412 may include a touchscreen display configured to allow a user to provide user input by interacting with graphical user interfaces displayed on the screen. The display may also be configured to display stimulation system data and stimulation therapy data received from one or more sensors.

The stimulation system 410 may comprise, for example, the neurostimulation systems including catheters with electrode structures and the like as described herein. Other tissue modulation systems, including for other indications other than treatment of heart failure, are also possible. For example, the denoising techniques and systems described herein may be used in conjunction with systems adapted to perform any one or more of the following: spinal neuromodulation, pacing with a pacemaker, defibrillation with an implantable defibrillator or external defibrillation system, pulsed electrocautery, stimulation of nerves to treat urinary or fecal incontinence, muscle stimulation, prostate stimulation, brain stimulation, stimulation of the vagus nerve, stimulation of osteoblasts, joint stimulation therapy to treat orthopedic conditions, iontophoresis, stimulation for tissue contact sensing, electroanatomical mapping, electrophysiology recording, etc. The denoising techniques and systems may also be used on conjunction with systems or devices employing motors, pumps, piezoelectric actuators, and/or the like. Interference sources that are synchronizable or periodic may be filterable or denoised using the techniques and systems described herein.

The stimulation system 410 may be configured to generate a programmable stimulation waveform to be applied to nerves of the subject 402 via one or more electrodes or other stimulation elements. The stimulation system 410 may optionally also include sensors (e.g., sensors on a catheter) to sense pressure (e.g., pulmonary artery pressure and right ventricle pressure) and receive signals indicative of the sensed pressure (as shown schematically in FIG. 4). The system 410 may also include sensors that directly sense electrical activity, such as cardiac electrograms or nerve activity. As discussed herein, application of electrical stimulation to a subject 402 can affect an ECG reading of the subject 402. The subject 402 is also connected to leads or leadwires of an ECG system 420 according to standard operation procedure to measure the rate and rhythm of heartbeats. Sometimes, an ECG amplifier (not shown) may optionally be used to amplify input signals from the ECG system 420.

The system 400 shown in FIG. 4 includes a denoising system 405 between the ECG system inputs 420 (e.g., electrodes, leads, leadwires, and/or processing hub) and the patient monitor 415. Instead of the patient monitor lead wire set 422 of the ECG system inputs 420 connecting directly to the patient 402, the ECG inputs 420 (e.g., two-channel 24-bit 800 Hz ECG system inputs converted to a 32-b it unsigned integer raw ECG) are connected to the inputs of the denoising system 415 through the patient monitor lead wire set 422 and the patient monitor 415 then connects to the lead wire set 424 output of the denoising system 405. The denoising system 405 is configured to capture and manipulate data from the ECG system inputs 420 prior to sending such data to an optional ECG amplifier or to the patient monitor 415 for display. In some implementations, the denoising system 405 comprises one or more filters (e.g., 50 Hz notch filter, 60 Hz notch filter, 50 Hz-60 Hz notch filter, Butterworth notch filter, adaptive filters using microcontrollers) to pre-filter typical 50 Hz line and/or 60 Hz line or 50 Hz-60 Hz or other line frequency component noise (and possibly harmonics) out of the ECG signals received from the ECG system inputs 420 or other analog front-end ECG system prior to modification (e.g., reconstruction, interpolation) during the denoising process so that values just prior to and after blanking and/or interpolation are known good values that do not include 50 Hz and/or 60 Hz or 50 Hz-60 Hz noise frequency components (e.g., 50 Hz and/or 60 Hz or 50 Hz-60 Hz or other line artifacts or spikes), thereby further enhancing signal fidelity. The one or more filters may include a bandpass filter (e.g., linear phase finite-impulse-response filter with a 3 dB cutoff of 0.05 to 40 Hz converted to signed 16-bit integers with a dynamic range of ±6.25 mV). The denoising system 405 can execute stored instructions or algorithms using one or more processors (e.g., computer circuitry or computing circuits) to perform a process or set of processing steps for denoising the ECG signals or the waveform generated and output for display. The denoising system 405 may include two signal outputs, one analog and one digital. The analog output provides denoised ECG signals to the patient monitor 415 for display. The analog output may have a unity gain or other gain values. The digital output provides a denoised ECG signal to the neuromodulation system 405. The denoising system 405 may also detect the QRS complex of the ECG and pass a corresponding marker to the neuromodulation system 410 for heart rate computation, stimulation synchronization, and/or other functions. The patient monitor lead wire set 422 could be replaced with other types of lead sets connected to other display and/or processing devices besides patient monitor 415, such as a central monitoring system.

The denoising system 405 can process multiple ECG input channels (e.g., 2, 3, 4, 5, 6, 7, 8, 9, 10 or more than 10 channels) and can support multiple ECG configurations. Not all channels are required to be used. In some examples, the stimulation system 410 or the ECG system 420 may comprise the denoising system 405 (e.g., the denoising system 405 may be a component or subsystem of the stimulation system 410 or the ECG system 420). In some implementations, the denoising system 405 is a separate, stand-alone component, or module, from the stimulation system 410 or the ECG system 420. The denoising system 405 can inhibit or prevent a neurostimulation waveform and/or the effects of neurostimulation on an ECG signal from corrupting an ECG signal, or portions thereof.

Figure 5A:
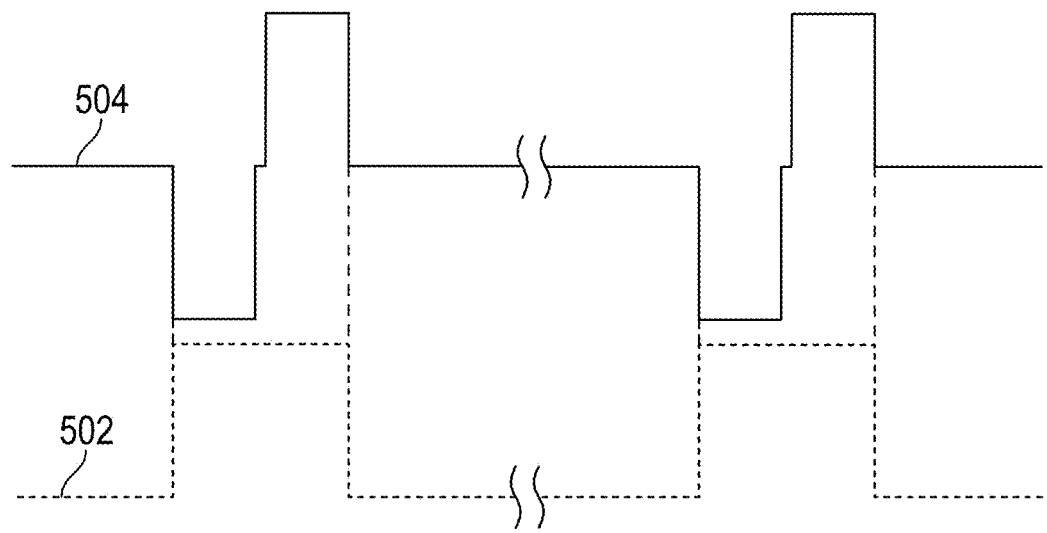
FIGS. 5A and 5B illustrate examples of timing diagrams of a blanking pulse signal and a stimulation pulse signal.

The denoising system 405 may receive stimulation timing information or data (e.g., time during which stimulation is applied) from the neuromodulation system 410 to facilitate the denoising process(es) (e.g., facilitate detection or identification of portions of the ECG signal or other physiological signal or biopotential that comprise noise or stimulation artifacts or are likely to comprise noise, such as stimulation artifact). In some implementations, the noise, or stimulation artifact, caused by an electrical stimulation system, for example, comprises periodic pulsatory type noise as opposed to random or continuous types of noise. The stimulation timing information may comprise a blanking pulse signal (e.g., synchronization pulse signal) 502 that is transmitted to the denoising system 405 coincident with the initiation of electrical stimulation pulses. The pulses of the blanking pulse signal 502 may advantageously be synchronized with the pulses of the stimulation pulse signal 504, as shown schematically in FIG. 5A. The first pulse of the blanking pulse signal 502 may indicate to the denoising system 405 that stimulation is about to begin, or is beginning, and therefore that the portions of the ECG signal corresponding to the time after the blanking pulse is received are likely to have temporary, or transitory, noise or interference (e.g., stimulation artifact) caused by application of electrical stimulation or other electromagnetic energy or fields and that those portions should be denoised by the denoising system 405. The blanking pulse may be continuously delivered (e.g., in a state indicative of an "on" or "active" condition) for the duration of the electrical stimulation (e.g., duration of each pulse cycle occurring during an electrical stimulation treatment period, which could last, for example, for several minutes, several hours, several days, or several weeks).

Figure 5B:
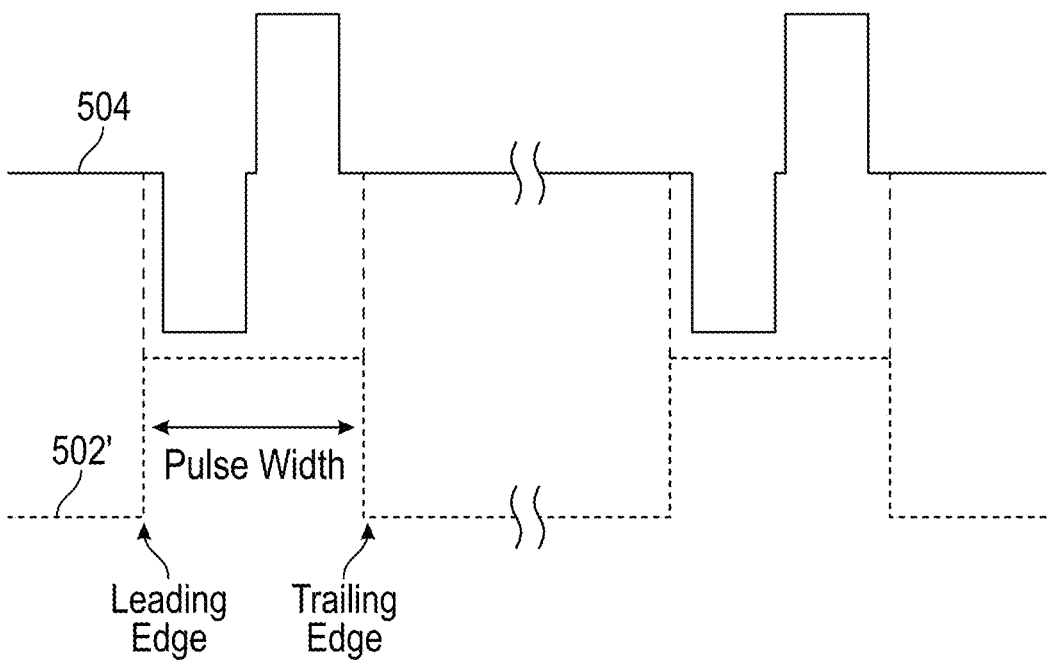

The pulses of the blanking pulse signal 502 may be used to identify, or detect, both the beginning and duration of the pulses of the stimulation pulse signal 504. This is true in principle but may require modifications in actual use. For example, it may be necessary in some implementations for the timing of the leading edge and trailing edge of the blanking pulses to be adjusted due to perturbations that lead or follow the stimulation artifact on the ECG waveform. FIG. 5B shows a blanking pulse signal 502' with modified leading and trailing edges. In several implementations, the leading edge of the first "on" pulse of the blanking pulse signal 502' is programmed or configured to occur a short time prior to the start of the first "on" pulse of the stimulation pulse signal 504 to allow for data acquisition and processing time inherent in the ECG signal path of the denoising system 405 and blanking pulse signal path. This leading offset value may be fixed as determined by the specifics of the internal denoising system 405 signal delays or adjustable to accommodate other encountered delay variables. For example, various implementations of the denoising system 405 and/or process 600, 605 may function best when the leading edges of the blanking pulses precede the leading edges of the stimulation pulses by a short period of time (e.g., 1-10 ms, 1-5 ms, 6-10 ms, 1 ms, 2, ms, 3 ms, 4 ms, 5 ms, 6 ms, 7 ms, 8 ms, 9 ms, 10 ms).

The trailing edge of the blanking pulse signal 502' may also advantageously extend beyond the trailing edge of the stimulation pulse signal 504 to account for distortion that may occur to the stimulation artifact as it appears on the ECG waveform. The electrical transfer function through the body between the implanted stimulation electrodes and the surface ECG electrodes can be complex, resulting in not only amplitude changes but in time delays of the stimulation artifact on the ECG waveform (e.g., spikes caused by stimulation) with respect to the stimulation pulses. In some implementations, the entire stimulation artifact is delayed (including initiation of the artifact and the ending of the artifact). The time delay at the end of the artifact causes the artifact trailing edge to lag the stimulation pulse trailing edge by a small amount. If the pulse width of the synchronization pulses (e.g., blanking pulses) is not extended to compensate for this effect, the entire artifact may not be blanked during the denoising process, thereby allowing some of the artifact spike to "leak" through. As with the synchronization pulse (e.g., blanking pulse) leading edge, the trailing edge offset may use a fixed value or be adjustable to accommodate variations in artifact distortion. The adjustable synchronization pulse (e.g., blanking pulse) leading or trailing edges may be implemented either as manually controlled functions by a user (e.g., based on artifact observed in the baseline of the denoised ECG signal) or determined automatically by methods or algorithms within the denoising system 405 or process 600, 605. In accordance with several implementations, because the denoising system 405 receives an indication in advance as to when stimulation is occurring as a result of receipt of the stimulation timing information (e.g., synchronization pulse), the denoising system 405 and processes 600, 605 can advantageously be deterministic and require less processing speed and/or computing resources. There may also be reduced signal latency compared to prior methods. The denoising processes and methods may be performed in real time (e.g., with minimal latency of less than 100 ms) such that the clinical professionals do not even realize that the denoising is being performed. In addition, the denoising system 405 and processes 600, 605 may advantageously not require linear circuit operation during noise artifact periods which makes it tolerant to signal saturation at those times.

The system 400 shown in FIG. 4 may further optionally comprise a physiological parameter determination subsystem or module. The physiological parameter determination subsystem or module may be an independent subsystem or module or may be a sub-component of the neuromodulation system 410 or the denoising system 405. The physiological parameter determination subsystem or module may be configured to, upon execution of instructions stored on a computer-readable medium by one or more processors, determine whether a physiological parameter being monitored (e.g., heart rate or other cardiac-related parameter, pressure within a cardiac-related vessel or chamber, such as a pulmonary artery or a ventricle) is outside of a threshold range. The threshold range may correspond to a predetermined acceptable safe range that does not cause alarm or require medical attention. The physiological parameter value may be determined based on signals received from one or more sensors coupled to tissue of a patient (e.g., R-R intervals determined from signals received from ECG leads coupled to skin of a patient) or positioned within a lumen or cavity of a patient (e.g., pressure values determined from pressure sensors positioned within a blood vessel or a heart chamber).

If the physiological parameter determination subsystem or module determines that the physiological parameter is outside the threshold range, the physiological determination subsystem or module may cause the neuromodulation system 410 to stop, or terminate, application of neuromodulation to the patient and may cause the denoising system 410 to be bypassed so as not to affect the ECG signals that no longer require denoising since the neuromodulation has been terminated. In some implementations, the physiological determination subsystem or module generates a control signal that is sent to the neuromodulation system 410 and/or to the denoising system 410. The physiological parameter determination subsystem or module may also comprise an alert generation subsystem or module configured to generate an alert or alarm event when the physiological parameter is determined to be out of range. The alert may be a visual alarm output to a display (e.g., on a patient monitor or on a display of a central monitoring system in a patient care facility). The alert may additionally or alternatively comprise an audible alert or alarm. The alerts may generate a text message, electronic mail message, page, or other warning message to a display of a central monitoring system of a health care facility or to a mobile communications device (e.g., pager, smartphone) of one or more individual caregivers. The alerts may be transmitted through wired connections or wirelessly (e.g., via Bluetooth or cellular data communication protocols or systems over a communications network). If the physiological parameter determination subsystem or module determines that the physiological parameter is within the threshold range, no action is taken and the neuromodulation system 410 and the denoising system 405 may continue to operate as normal.

Figure 6:
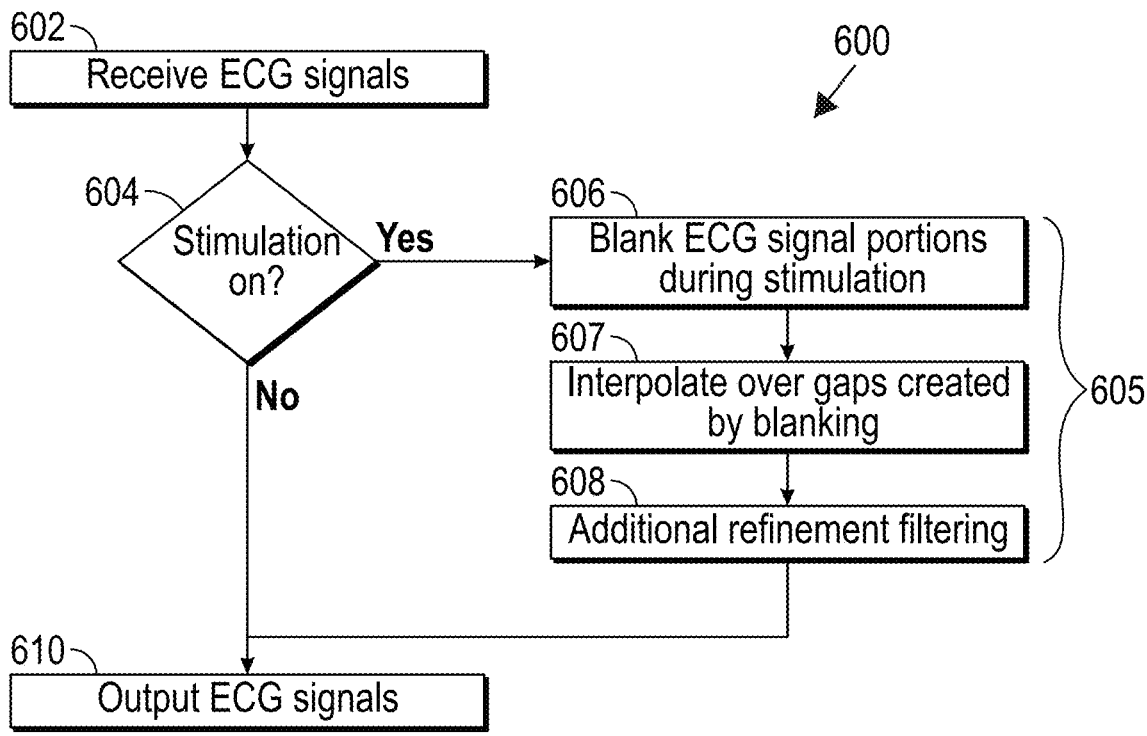
FIG. 6 schematically illustrates an example method of denoising an ECG signal when electrical stimulation is being applied by a stimulation system.

With reference to FIG. 6, an example of an algorithm or process 600 of denoising ECG signals or waveforms performed by the denoising system 405 is schematically illustrated. The denoising system 405 can execute stored instructions or algorithms using one or more processors (e.g., computer circuitry or computing circuits) to perform the process 600. At Block 602, the various ECG signals are received directly from the ECG sensors, or from the ECG system inputs 420. At decision Block 604, the denoising system 405 determines whether stimulation or other electromagnetic energy is currently being applied. In accordance with several implementations, the process 600 advantageously does not apply filtering (e.g., blanking and modifying (e.g., reconstructing, interpolating) to the entire ECG waveform. Instead, the process 600 applies filtering only to portions of the ECG waveform likely to have stimulation artifacts, thereby leaving those portions that are free (or substantially free) of stimulation artifact unaffected and unmodified. In some examples, the denoising system 405 can receive a signal from the neuromodulation system 410 when the neuromodulation system 410 is applying neurostimulation through a physical electrical connection (e.g., the blanking pulse signal 502 described above). The denoising system 405 may be configured to correlate the time of receipt of the signal indicative of application of neurostimulation therapy or other modulation or electromagnetic energy with the timing of the ECG signals so as to know which portions of the ECG signals comprise, or are likely to comprise, noise or interference (e.g., stimulation artifacts).

In some implementations, a synchronization blanking pulse signal may not be used and the determination of whether stimulation is being applied is independently determined by the denoising system 405 based on an analysis of the ECG waveform to predict or determine whether stimulation is being applied and/or to generate a synchronization (e.g., blanking) pulse signal, or signal indicative of stimulation being applied. The synchronization (e.g., blanking) pulse signal can be generated from the stimulation-corrupted ECG signal directly, thereby eliminating the need for a separate synchronization pulse (e.g., blanking pulse). Because the stimulation signal, and hence the artifact, are periodic, they can be extracted from the original ECG signal using one or more clock extraction techniques, such as autocorrelation, or by using a phased locked loop (PLL). Additional methods can be employed to determine the correct blanking pulse width and the optimal phase relationship to use with the stimulation signal. Once these values are determined they can be saved and quickly reapplied for successive stimulation pulses. If the stimulation parameters change, the denoising system 405 can once again determine the correct denoising parameters to apply. This "extracted blanking pulse" technique could be useful, for example, in circumstances where a denoising function is applied to a system not originally designed to provide a synchronized blanking pulse signal.

As another example, a peak detector (e.g., 20 Hz peak detector) could be used in combination with other methods or techniques to detect the presence of noise caused by the neuromodulation system 410 as an indicator of whether electrical stimulation or other modulation is being applied at the current time. In various implementations, different wireless synch (including optical links), wired synch or synch generation techniques may be used. For example, a wireless connection such as Bluetooth or a number of other means can also be used in place of a physical electrical connection.

If it is determined at decision Block 604 that stimulation is being applied, then a denoising sub-process 605 is initiated by the denoising system 405. For example, the blanking pulse signal 502 from the neuromodulation system 410 can open a circuit to interrupt the direct connection between the ECG system 420 and the patient monitor 415 and instead direct the original corrupted ECG signal to the denoising system 405. If it is determined at decision block 604 that stimulation is not being applied, then the ECG waveform can be output for display at Block 610 as normal without going through the denoising sub-process 605. When no signal indicative of stimulation being applied is received from the neuromodulation system 410, the circuit between the ECG system 420 and the ECG amplifier 425 can be re-closed and the denoising system 405 may be bypassed. In other words, the ECG signals are not directed through the denoising system 405 and are processed without going through the processing of the denoising system 405. The denoising system 405 can include multiple switches that can be triggered (change the state between open and closed) depending on the determination of whether or not stimulation is being applied (and thus, whether the denoising system 405 should be bypassed or not). For example, when the ECG input signals are bypassing the denoising stages, normally closed switches between each ECG channel input and corresponding channel output can be used to pass the ECG signals directly to the output of the denoising system 405 without any filtering or signal modification. When the denoising sub-process 605 is active, the state of the switches may be changed to direct the ECG input signals to the denoising circuitry stages.

Figure 7A:
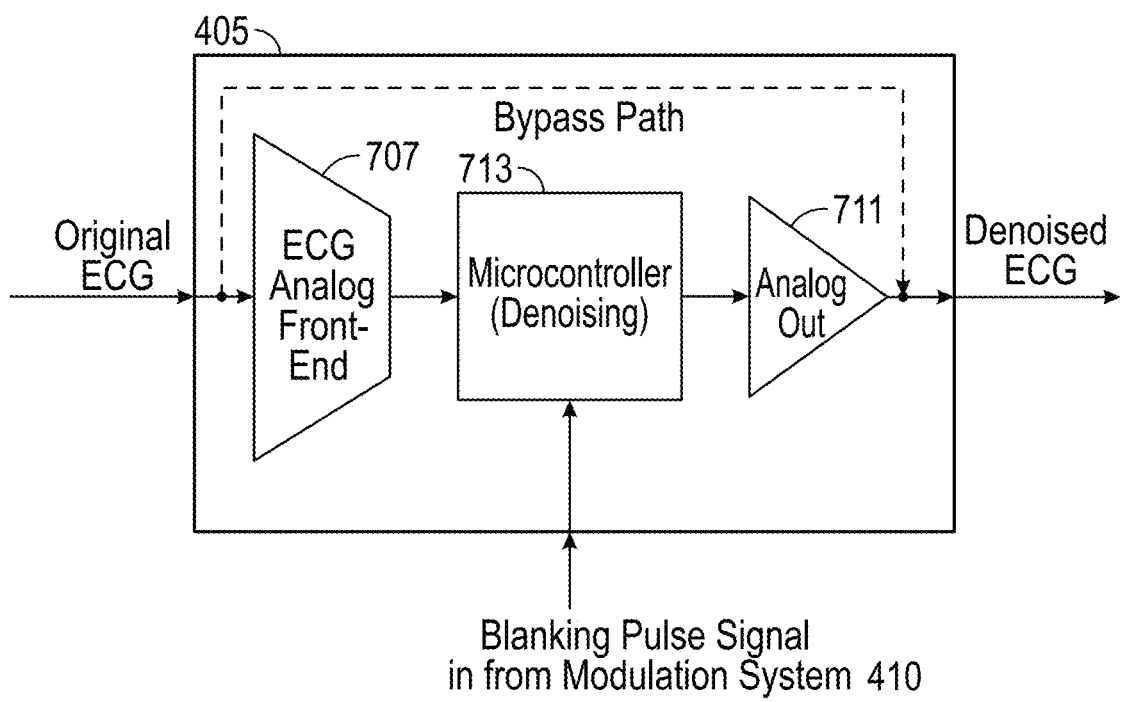
FIG. 7A schematically illustrates a bypass signal path and examples stages of the denoising system.

In implementations where a blanking or other synchronization pulse signal is generated, the denoising process 500 may be treated as a system-level operation because the neuromodulation system 410 not only generates a stimulation therapy signal but also generates the synchronization pulse signal that facilitates the denoising 600 (e.g., denoising sub-process 605). Turning briefly to FIG. 7A, an example of a bypass path in which at least the major stages of the denoising sub-process 605 (e.g., ECG analog front-end stage, which may include an analog-to-digital-converter and/or amplifier, a microcontroller that performs the denoising sub-process, and an analog out stage, which may include a digital-to-analog converter and/or amplifier) are bypassed.

Turning back to FIG. 6, the denoising sub-process 605 may include multiple processing steps. At Block 606, the portions of the ECG waveform or signals that are likely to include artifact spikes or interference noise during stimulation (as determined by, or as detected or identified based on the stimulation timing information or data received from the neuromodulation system 410) may be "blanked" from the ECG waveform or signals (e.g., during a determined blanking period or window). The components of the denoising sub-process may be performed on all of the portions or components of the ECG waveform or signals identified or detected as having noise (e.g., during the duration of each stimulation or other modulation pulse cycle) at the same time (e.g., simultaneously) or may be performed on each portion separately (e.g., sequentially).

The denoising sub-process 605 may be performed for the entire length of stimulation (e.g., the whole time the blanking pulse is in a state indicative of stimulation being "on" or "active") or for a portion of stimulation. The denoising sub-process 605 may or may not be performed during the time (either all or a portion of the time) of the blanking pulse that occurs prior to actual stimulation. For example, if the first blanking pulse is received 4 ms prior to actual stimulation, the denoising sub-process 605 may start after 4 ms or after a time less than 4 ms (e.g., 2 ms, 3 ms, 1 ms). In one implementation, the "blanking" may involve application of one or more decimation filters to permanently eliminate data points during the time of stimulation (e.g., by performing down sampling), thereby resulting in a data set that is smaller in size than the original data set. The eliminated data points (e.g., data values and certain memory locations) may not be replaced in these implementations. However, the decimated data points could be reinserted with new data points whose values are calculated during a subsequent interpolation step. Under this approach, the final data set would once again be larger and match the size of the original data set prior to decimation. In another implementation, data points at various intervals (e.g., memory locations) are not permanently eliminated during the blanking step but are preserved and values at the data points are modified or substituted with different values (e.g., value of the preceding or succeeding memory location, or a mean of the values in preceding and/or succeeding memory locations, or a value between the value in the preceding and/or succeeding memory location) during a subsequent interpolation step. Because the denoising sub-process 605 removes the stimulation artifact through blanking, even artifacts that saturate the analog channel can be successfully removed or modified without adversely impacting the underlying ECG waveform. The blanking may include compressed, saturated, or clipped portions of the ECG signals. The ECG signals may be digitized prior to or at Block 606 using digitizing circuitry, such as an analog-to-digital converter (ADC). The digitized ECG signals may also be amplified.

At Block 607, interpolation or other modification or reconstruction may be performed to fill in the gaps (e.g., insert straight or curved line segments to connect the dots) created by the blanking performed at Block 606. In some implementations, interpolation involves taking a last known good value prior to blanking and duplicating that value at all data points during the blanking window. The interpolation may involve taking the last known good value prior to blanking and the first known good value after blanking and interpolating between those two values to insert interpolated values at data points or memory locations during the blanking. In some implementations, interpolation may simply involve inserting the last known good value prior to blanking and inserting that same value in all of the memory locations during the blanking. If decimation was performed in the blanking step, the decimated locations (e.g., data points) could be reinserted with new data points whose values are calculated using interpolation filters or techniques. If no decimation was performed in the blanking step, the values at the existing data points may simply be replaced using interpolation filters or techniques. In both implementations, the final data set may be the same size as the initial data set—the difference being that if decimation is performed, new data points are added to replace data points removed during decimation (which may involve down-sampling) and if decimation is not performed, no new data points are added). Interpolation filters and digital filtering techniques may be used to perform the interpolation (including finite-impulse-response (FIR) filters or adaptive filters). Interpolation may include up-sampling (e.g., if decimation was performed during the blanking step). Refining filtering techniques may then optionally be applied at Block 608 to smooth out the final waveform (or preserve the general original waveform appearance) for display. In some implementations, refining comprises application of a linear phase filter. In one example, band pass filtering is performed using a linear phase FIR filter with a 3 dB cutoff of 0.05 Hz to 40 Hz and converted to signed 16-bit integers with a dynamic range of +/−6.25 mV. In some implementations, a 40 Hz low pass filter is used. In some implementations, the denoising sub-process 605 may involve decomposing the digitized ECG signals into subcomponents in different domains (e.g., time domain and frequency domain). The optional additional filtering at Block 608 may also include detection of R waves. The R-wave detection may be sent to the neuromodulation system 410. The signals may be converted from digital to analog signals at or following Block 608 (e.g., using a digital-to-analog converter) and before output for display at Block 510.

In some implementations, the filters involved in the denoising sub-process 605 introduce a slight signal delay (e.g., 5-20 ms, 10-20 ms, 15-25 ms, 15-17 ms, overlapping ranges thereof, or any value within the recited ranges). Use of an optional digital-to-analog converter may add even more latency. In accordance with several implementations, total delay and latency is less than 100 ms (e.g., less than 90 ms, less than 80 ms, less than 70 ms, less than 60 ms, less than 50 ms, less than 40 ms, less than 30 ms, less than 25 ms). The modifications to the timing of the blanking pulse signal 502 described above in connection with FIG. 5B may help to account for the latency and delay of the denoising sub-process 605.

In some implementations, the process 600 includes additional sub-processes. In some implementations, stimulation or delivery of electrical modulation by the neuromodulation system 410 is halted if measured parameters (e.g., R-R intervals or relevant vessel or chamber pressures determined by the pressure sensors of the neuromodulation system 410) are determined to be out of the acceptable safe range, and the denoising sub-process 605 is bypassed. For example, the process 600 may include a threshold preliminary sub-process (which may be carried out by the physiological parameter determination subsystem or module described above in connection with FIG. 4) that analyzes the input ECG waveform or signals and determines an R-R interval (a single R-R interval or an average R-R interval). If the R-R interval is determined to be too short or too long (e.g., below or above a threshold indicative of tachycardia, bradycardia, or other abnormal heart rhythm condition), the process 600, via an alert generation subsystem or module, may generate a control signal that is sent to the neuromodulation system 410 to automatically terminate modulation (e.g., stimulation) for safety reasons. Alternatively, an alert (e.g., audible, visible alert or alarm event) could be generated to prompt the clinician to manually terminate stimulation. If the R-R interval is determined to be within an acceptable "safe" range, then the process 600 may continue to the denoising sub-process 605. Hospital monitors' first level of detection can be based on R-R intervals, which are not impacted (not significantly impacted) by the denoising processes described herein.

Another optional sub-process that may be performed prior to the denoising sub-process 605 includes detection of pacemaker pulses on the ECG waveform or signals. This sub-process may involve stripping out the pacemaker pulses and reinserting them in the ECG waveform after the denoising sub-process 605. In some implementations, the process 600 may involve execution of a lead-off detection module or sub-process that triggers errors that generate a "lead off" condition if impedance measurements are outside a threshold range. The errors may result in generation of an alert, using an alert generation subsystem or module, that something is wrong that may require attention. In some implementations, the alerts may include indication of loss of contact between a sensor and tissue or between a stimulation electrode of the modulation system 410 and tissue (e.g., based on impedance and/or force measurements) or indication of catheter migration based on a determined real-time position of a component (e.g., catheter tip, stimulation electrode, sensor) of the modulation system 410. Such alerts may be based on a detection of changes in stimulation artifact characteristics. The various alerts described herein may be audible and/or visible. The alerts may generate a text message, electronic mail message, page, or other warning message to a display of a central monitoring system of a health care facility or to a mobile communications device (e.g., pager, smartphone) of one or more individual caregivers. The alerts may be transmitted through wired connections or wirelessly (e.g., via Bluetooth or cellular data communication protocols or systems over a communications network). Another sub-process of process 600 may include the actual treatment of the patient using the neuromodulation system 410 by applying electrical stimulation to nerves to treat acute heart failure.

In some configurations, a pre-filtering sub-process may optionally be performed prior to or during the denoising sub-process 605. The pre-filtering sub-process may be performed prior to or during Block 606. The pre-filtering sub-process may include application of a notch filter or adaptive filter adapted to filter out 50 Hz and/or 60 Hz noise (e.g., typical 50 Hz and/or 60 Hz line frequency or 50 Hz-60 Hz frequency components) from the ECG signals or other biosignals received by the denoising system 405. The pre-filtering sub-process may advantageously provide smoothing of the signals around the "blanking" window (e.g., before and/or after the blanking window) to further enhance interpolation during the denoising sub-process 605 due to the absence of 50 Hz and/or 60 Hz noise artifacts otherwise present on the signals or waveform during the blanking window. In some implementations, the pre-filtering sub-process comprises application of a moving average window before and/or after the blanking window to smooth out the portions of the signals passed on to the blanking and interpolation sub-processes.

Figure 7B:
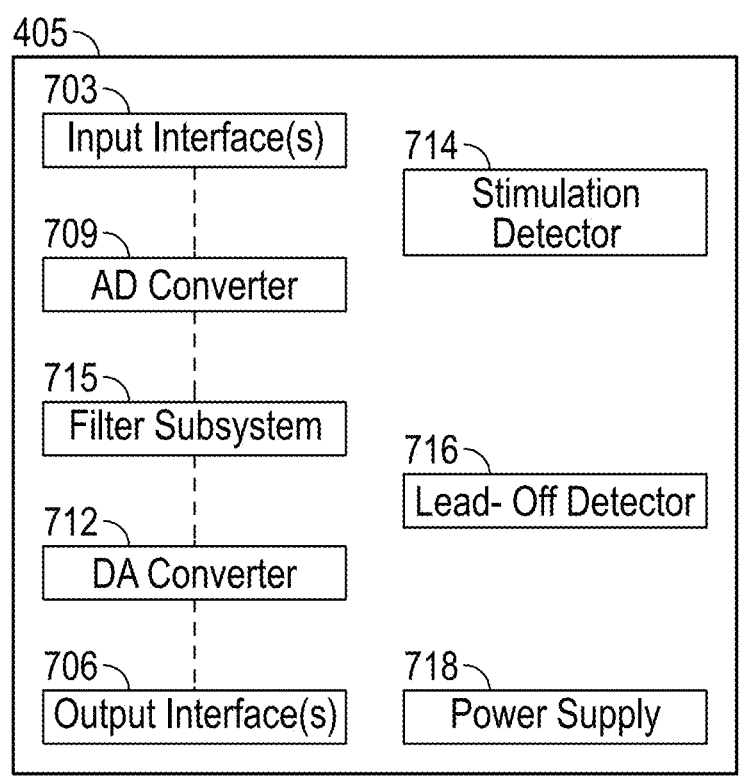
FIG. 7B schematically illustrates example components of the denoising system.

FIG. 7B schematically illustrates example components of the denoising system 405. The denoising system 405 includes one or more input/output interfaces, ports, or modules. The input/output interfaces may include one or more input interfaces 703 and one or more output interfaces 706. The input interfaces 703 may include an ECG lead input interface through which the signals from the ECG system 420 (e.g., including sensors and leads and a processing hub) are received and/or a stimulation timing input interface through which stimulation timing information or data is received from the neuromodulation system 410. The denoising system 405 may optionally include a stimulation detector module or subsystem 714 that is configured to determine whether stimulation, or other modulation, is being applied that is causing unwanted interference or noise (e.g., stimulation artifact) on the ECG waveform. As described above, the stimulation detector module or subsystem 714 can detect stimulation based on a received blanking pulse signal or based on analysis of the ECG signals or waveform without receiving a blanking pulse signal. In some implementations, the blanking pulse signal 502 is received from the neuromodulation system 410 as a logic level signal via a micro USB connector and an optical isolator. The denoising system 405 may provide real-time detection of the R-wave and communicate a logic-level signal corresponding to the R-wave peak to the neuromodulation system 410 via the micro USB connector. The denoising system 405 may also include an analog-to-digital converter (ADC) 709 that digitizes the received analog ECG signals for signal processing purposes and a digital-to-analog converter (DAC) 712 that converts the processed and filtered digital signals back to analog signals. The ECG analog front-end stage 70 of FIG. 7A may include one or more of the input interface(s) 703, the stimulation detector 714, the lead-off detector 716, and ADC 709. The filter subsystem 715 may include the microcontroller 713 of FIG. 7A and/or the stimulation detector 714. The analog out stage 711 of FIG. 7A may include one or more of the DAC 712 and output interface(s) 706.

The denoising system 405 further includes a filter subsystem 715 that performs various signal processing functions to remove the noise from the ECG waveform. The filter subsystem 715 may include a blanking subsystem or module and an interpolation subsystem or module, and may optionally include additional refining filtering subsystems or modules (such as the pre-filtering subsystems or modules to remove typical 50 Hz and/or 60 Hz line or 50 Hz-60 Hz frequency components prior to blanking and/or interpolation described herein). The blanking subsystem or module is configured to, upon execution of instructions stored on a non-transitory computer readable medium, blank selected data values of selected portions of the digitized signal corresponding to the time during which stimulation was, or is being, applied. In some implementations, the data values at selected memory locations are preserved and modified to new data values that replace the temporarily removed data values during subsequent interpolation. In some implementations, the blanking subsystem or module is configured to perform decimation, whereby selected data points corresponding to portions of the digitized signal identified as having transitory noise (e.g., stimulation artifact) are eliminated (e.g., down-sampled), and then perform up-sampling to pad with new data points of selected values. The blanking subsystem or module configured to reduce a sampling rate of the digitized ECG signal (e.g., to reduce the computational complexity) to reduce the number of data points during the identified, or detected, stimulation periods in either approach. The blanking subsystem or module may perform anti-aliasing filtering and may include a low pass filter with a particular cutoff frequency. The interpolation subsystem or module is configured to fill in the gaps created by blanking during the stimulation periods. For example, in some implementations, the interpolation subsystem or module captures a last data point (e.g., last known good value) prior to blanking and a first data point (e.g., first known good value) after the blanking and then interpolates between these two data points. In some implementations, the interpolation subsystem or module may duplicate a value of the last known good data point prior to blanking and duplicate that value in all of the data points during the blanking period or window. The interpolation subsystem or module may increase the sampling rate of the digitized signal to add back in (e.g., pad) samples that were removed during decimation or fill in the data values at data points that were preserved during blanking with new modified values based on interpolation in order to make the signal more accurate and smooth. The interpolation may include performing one or more of linear, curvilinear, and cubic spline interpolation, as well as other interpolation techniques.

Although the denoising sub-process 605 (e.g., blanking and interpolating techniques) have been described as being implemented in the digital domain with digital signal processing techniques, the denoising sub-process 605 may also be implemented with similarly useful results in the analog domain. For example, one such approach involves use of a unity gain amplifier (or amplifier with other gain values) and then the denoising system 405 is configured to sample and hold at a steady or fixed voltage level at the time the blanking pulse signal 502 is received and then return to unity gain or other gain value when the blanking pulse signal 502 is no longer being received (e.g., is no longer in an active state indicative of stimulation being applied). The transient that might occur as a result could be filtered to provide smoothing. In accordance with several implementations, a method of denoising an ECG waveform obtained from a patient, wherein the ECG waveform comprises transitory noise caused by application of electrical stimulation by an electrical stimulation system located within or adjacent the patient, includes receiving a synchronization pulse (e.g., blanking pulse) from the electrical stimulation system indicative of initiation of stimulation by the electrical stimulation system and removing the transitory noise from the ECG waveform based upon the received synchronization pulse using an analog-based approach. The analog-based approach may include applying a unity gain amplifier (or amplifier with other gain values) to an input analog ECG signal, sampling a voltage level of the input analog ECG signal at a first time instance corresponding to the received synchronization pulse, and holding at the voltage level until the synchronization pulse transitions to a state indicative of termination of stimulation by the electrical stimulation system.

The optional additional refining filtering subsystem or modules may include a linear phase filter (e.g., achieved using a finite impulse response filter). The linear phase filter may advantageously make re-creation of the wave shape of the original ECG input signal feasible (e.g., such that morphology of the ECG waveform is not significantly impacted by the denoising system 405 and processes). In one implementation, band pass filtering is performed using a linear phase FIR filter with a 3 dB cutoff of 0.05 Hz to 40 Hz and converted to signed 16-bit integers with a dynamic range of +/−6.25 mV. In one implementation, the additional filtering subsystem or modules may include a 40 Hz low pass filter prior to being routed to the denoising system output lead wires 424, thereby providing a connection point to the patient monitor 415. However, other filters or filtering techniques in the digital and/or analog domain may be used as desired and/or required. For example, a Butterworth filter may be used in certain implementations. Chebyshev filters or other filters or filtering techniques (e.g., a Wiener filter, a morphological filter) may also be used as desired and/or required. In some implementations, no additional filtering is required after interpolation or other modification or reconstruction. For instance, the ECG monitoring systems may itself include a band pass filter on the front end that can eliminate any residual transitory noise (e.g., stimulation artifact) following interpolation. The additional filtering subsystem or module may include a notch filter or adaptive filter to remove 50 Hz and/or 60 Hz or 50 Hz-60 Hz frequency components or noise prior to blanking and/or interpolation.

The denoising system 405 may also include a lead-off detector module or subsystem 716 configured to monitor contact impedance measurements and detect when one of the ECG leads is not properly attached or connected (and thus not generating accurate data) based on the monitored contact impedance measurements. The denoising system 405 may further include a power supply 718 adapted to power the components of the denoising system 405. The power supply 718 may include a battery, capacitor, or other energy storage device. The power supply 718 may be rechargeable.

Figure 8C:
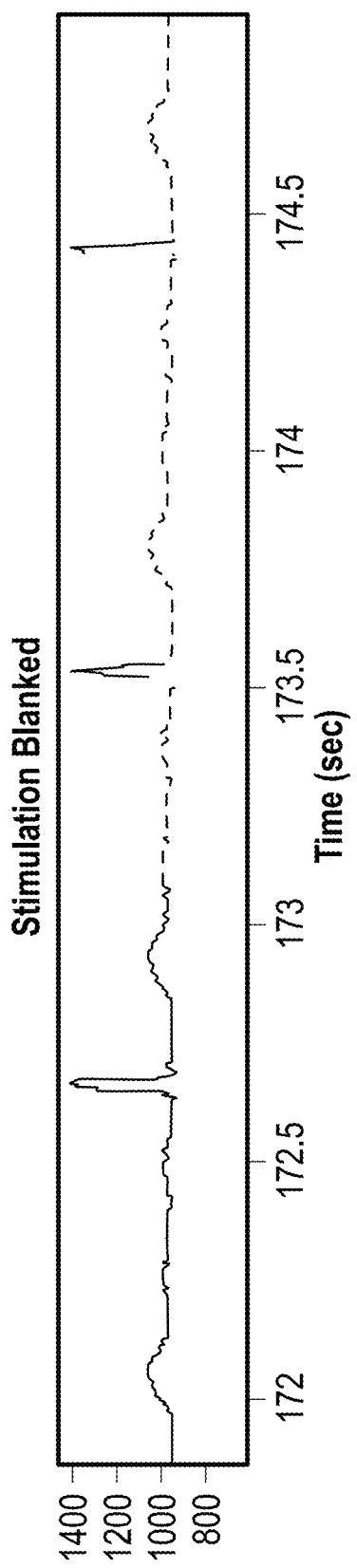
FIG. 8C schematically illustrates the example ECG waveform of FIG. 8B after blanking performed by the denoising system.
Figure 8D:
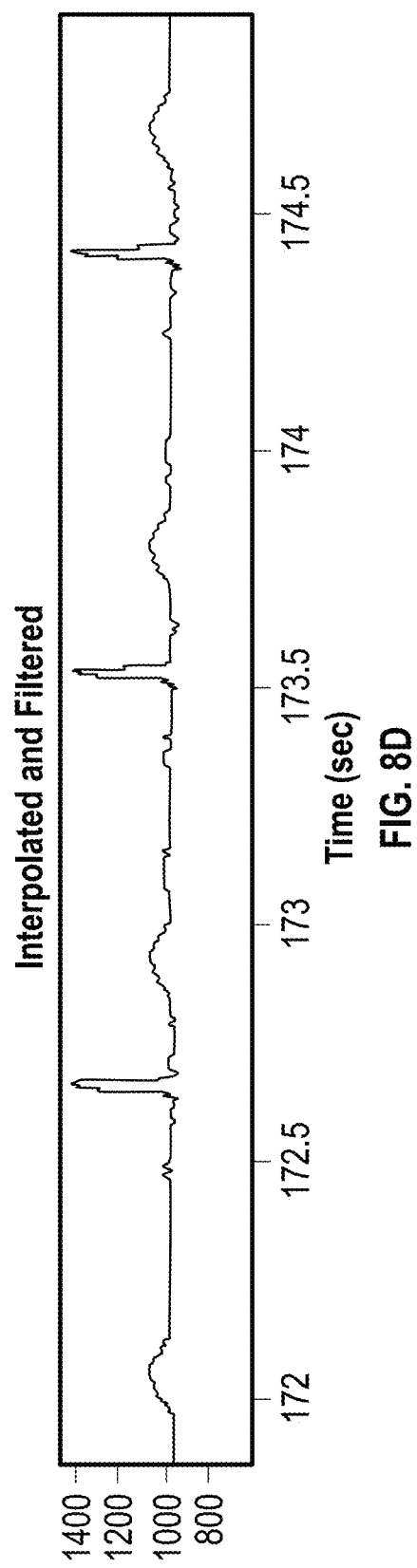
FIG. 8D schematically illustrates the example ECG waveform of FIG. 8C after interpolating and optional refining performed by the denoising system.

FIGS. 8A-8D help schematically illustrate the effects on the ECG waveform at various steps of denoising processes, such as those described herein. FIG. 8A illustrates an example clean ECG waveform without any noise (e.g., when electrical stimulation is not being applied). FIG. 8B illustrates the same ECG waveform but at a time during electrical stimulation when the noise or interference caused by the electrical stimulation (e.g., stimulation artifact) is visible on the ECG waveform. FIG. 8C schematically illustrates the ECG waveform of FIG. 8B after a blanking step is performed by the denoising system 405. As can be seen in FIG. 8C, the spikes caused by the stimulation have been removed from the ECG waveform. FIG. 8D schematically illustrates the example ECG waveform of FIG. 8C after interpolating and additional filtering steps are performed by the denoising system 405.

Figure 9C:
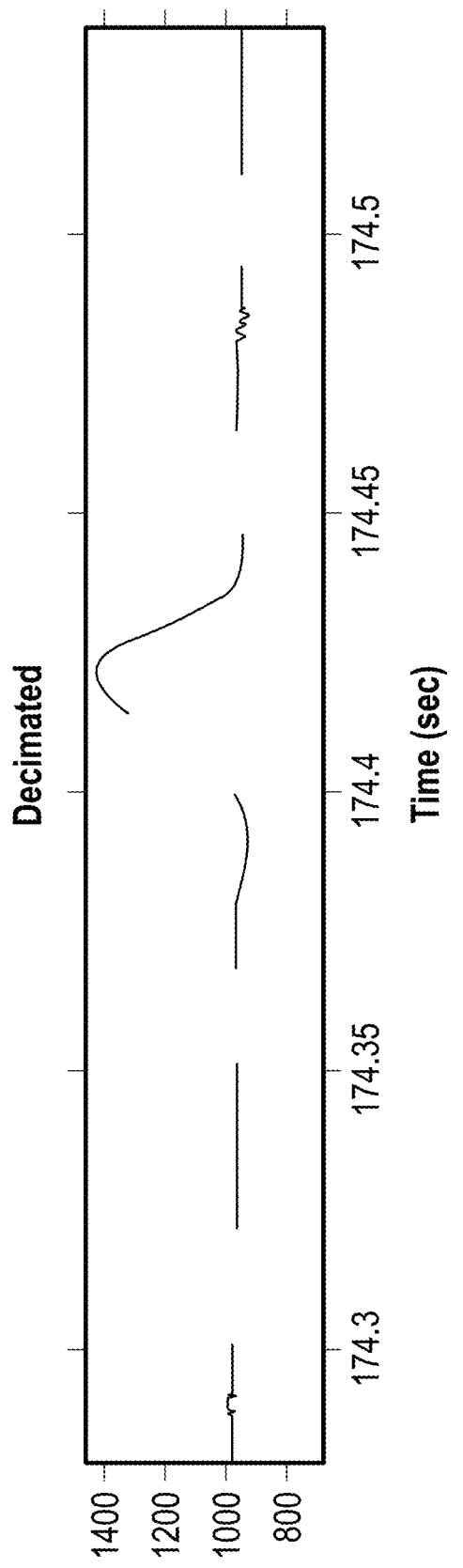
FIGS. 9C and 9D schematically illustrate the portion of the example ECG waveform of FIG. 9B after blanking (FIG. 9C) and interpolating and optional refining (FIG. 9D) performed by the denoising system.
Figure 9D:
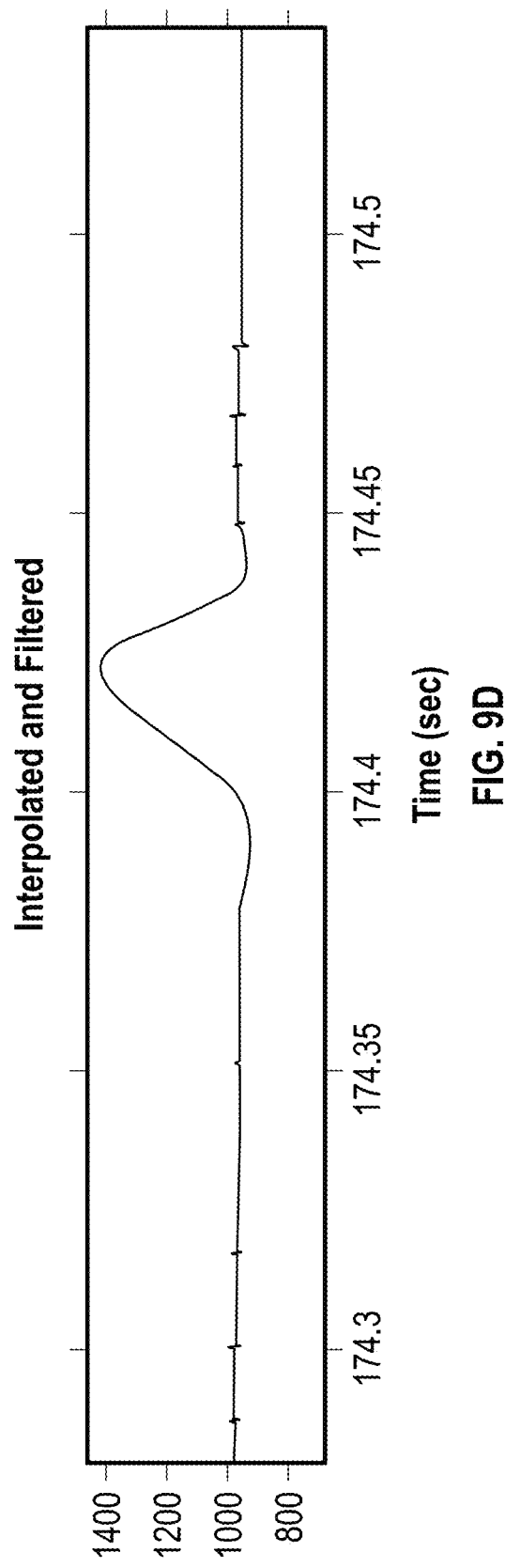

The accuracy of the blanking and interpolation steps of the denoising sub-process 605 are illustrated better with a zoomed-in view of the portions of the waveforms with the stimulation artifact. FIGS. 9A-9D illustrate close-up, exploded views of a portion of the corresponding ECG waveforms of FIGS. 8A-8D. The portion of the ECG waveforms in FIGS. 9A-9D is the portion indicated by the rectangle overlaid over the waveform toward the right end of FIG. 8B. This portion represents a portion of the ECG waveform correlating to a time period surrounding a single heart beat. For example, FIG. 9A, which shows a portion of a clean ECG waveform without any noise (e.g., when electrical stimulation is not being applied), includes only a single QRS complex. FIG. 9B illustrates how the same portion of the ECG waveform as in FIG. 9A appears during application of electrical stimulation when the noise or interference caused by the electrical stimulation is visible on the ECG waveform. The stimulation spikes surrounding the QRS complex caused by the electrical stimulation are clearly visible in FIG. 9B. FIGS. 9C and 9D schematically illustrate the same portion of the example ECG waveform of FIG. 9B after blanking or decimation (FIG. 9C) and interpolation and additional filtration (FIG. 9D) steps are performed by the denoising system 405. FIG. 9C shows how the initial lead up portion of the QRS complex can be blanked and then recreated in FIG. 9D using interpolation and additional filtering without compromising fidelity or morphology of the original ECG waveform.

The denoising processes and systems described herein can advantageously and successfully be used to denoise ECG signals not only when a heart is in normal sinus rhythm but also when the heart is experiencing abnormal heart rhythms or rates (e.g., arrhythmia, bigeminy, trigeminy, atrial fibrillation, ventricular fibrillation, tachycardia, bradycardia, etc.). Thus, accurate patient diagnoses can advantageously be made even when the denoising processes are being performed. For complicated heartbeats (e.g., premature ventricular contraction (PVC), bigeminy, etc.), other ECG signal manipulation may be used. Bench testing was performed to evaluate fidelity and performance of the denoising processes described herein. Stimulation spikes were extracted from surface recordings obtained during animal stimulation testing (e.g., using sheep animal models). These extracted stimulation spikes were superimposed on stored human ECG waveforms from a database. The original ECG waveform and the denoised ECG waveforms after application of the denoising processes described herein were compared. The denoising methods were found not to have an appreciable impact on morphology or fidelity of the ECG waveforms, as shown, for example in FIGS. 10A-13B. FIGS. 10B, 11B, 12B and 13B show comparisons of the original ECG waveforms and the denoised ECG waveforms for various heart rhythms. For example, the mean quality of signal reconstruction (QSR) may be greater than or equal to 95% (greater than or equal to: 95%, 96%, 97%, 98%, 99%) for the denoised ECG waveforms (e.g., for the entire waveform or signal, for the QRS waves, and/or for the P-T waves), where QSR is determined by the following equation:

$$QSR = 100\% \left\{ 1 - \frac{\sum_{i=1}^{N}(ECG_{Clean} - ECG_{Filtered})^2}{\sum_{i=1}^{N}(ECG_{Clean})^2} \right.,$$

where $ECG_{Clean}$ is the data set prior to stimulation pulse interference and where $ECG_{Filtered}$ is the stimulation corrupted data set after the denoising process 600. Tests of data sets with normal rhythms and data sets with arrhythmias including bigeminy, atrial fibrillation, and ventricular fibrillation described above resulted in QSR values between 99.16% and 99.63%.

Figure 10A:
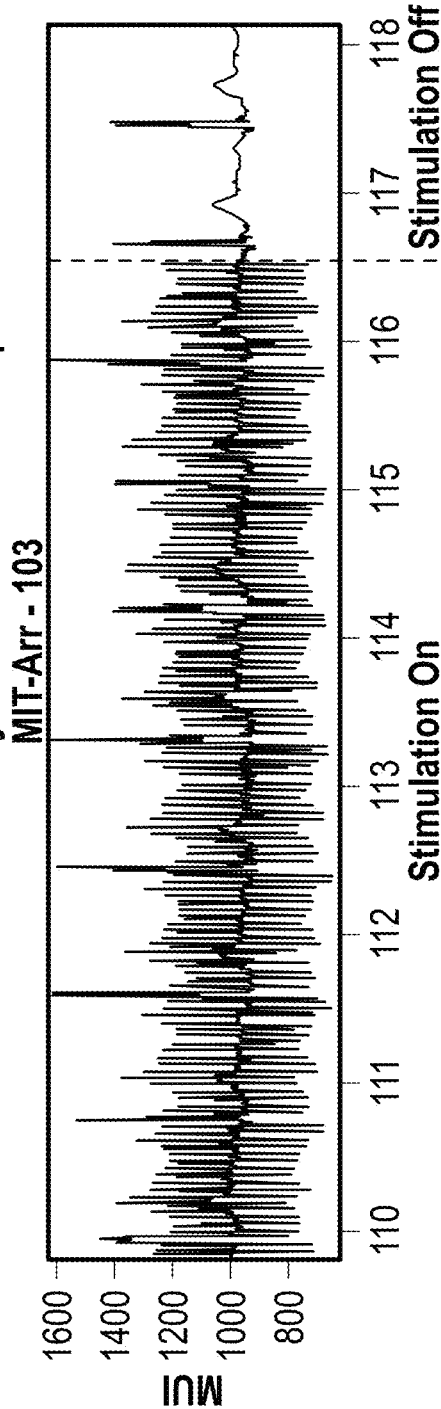
FIGS. 10A and 10B illustrate a normal sinus rhythm ECG waveform during application of neurostimulation without denoising and with denoising, respectively.
Figure 10B:
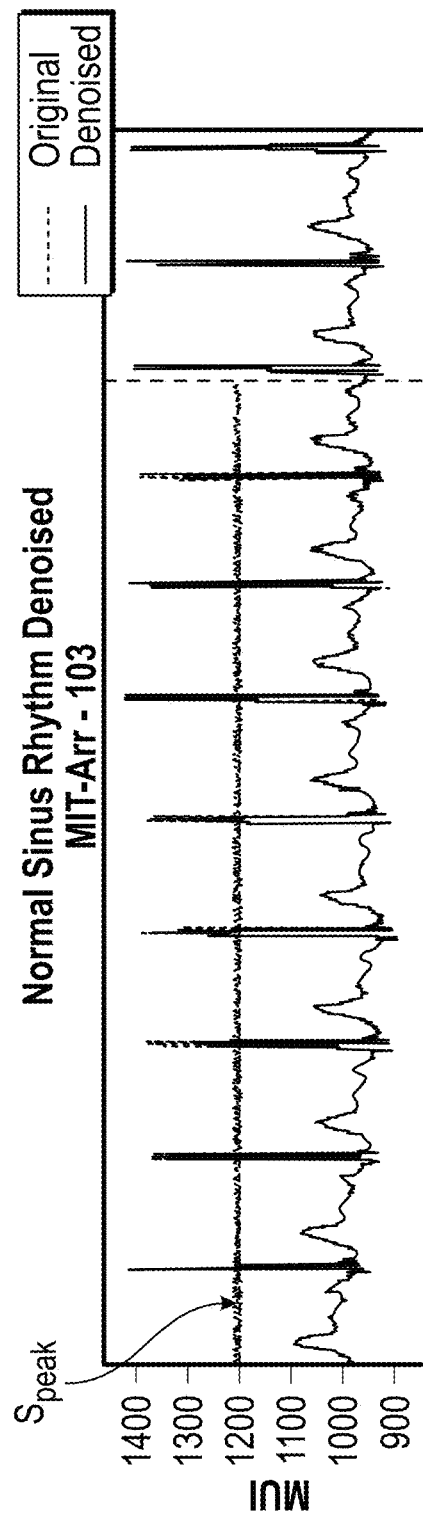

FIGS. 10A and 10B illustrate a normal sinus rhythm ECG waveform during application of neurostimulation without denoising and with denoising, respectively. As shown, the pronounced T and P waves are not impacted (or not significantly impacted) by the denoising process. The line $S_{peak}$ in FIG. 10B indicates the location of the original stimulation artifact, or transitory noise, spikes from FIG. 10A prior to denoising.

FIGS. 11A and 11B illustrate an ECG waveform indicative of bigeminy during application of neurostimulation without denoising and with denoising, respectively. Again, the line $S_{peak}$ in FIG. 11B indicates the location of the original stimulation artifact, or transitory noise, spikes from FIG. 11A prior to denoising.

Figure 12A:
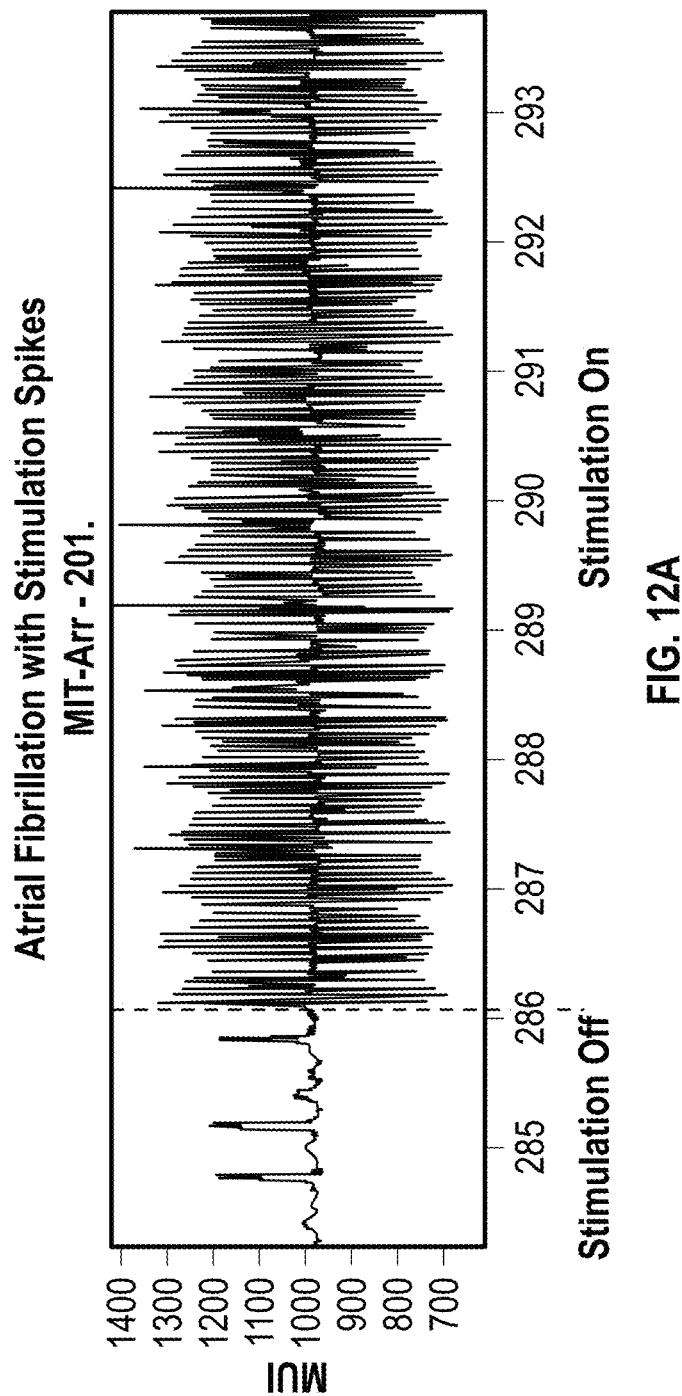
FIGS. 12A and 12B illustrate an ECG waveform indicative of atrial fibrillation during application of neurostimulation without denoising and with denoising, respectively.
Figure 12B:
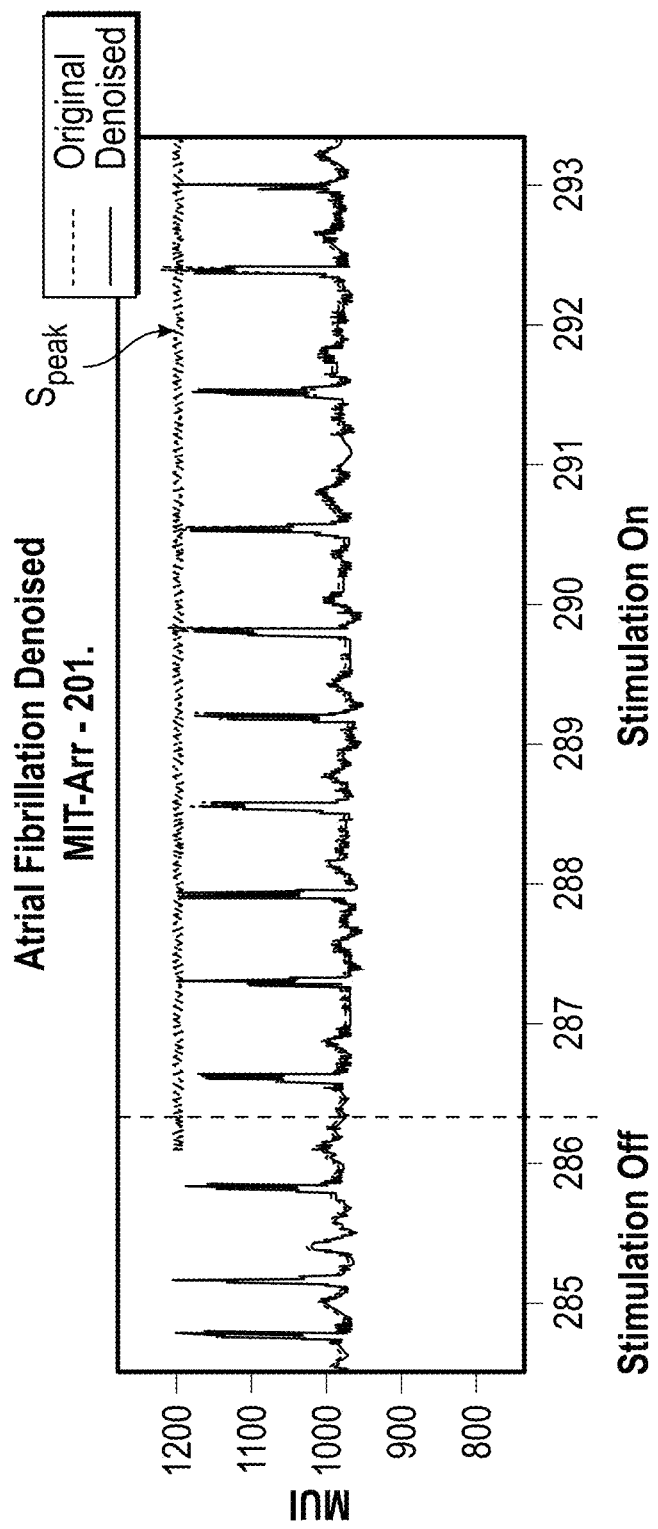
Figure 13A:
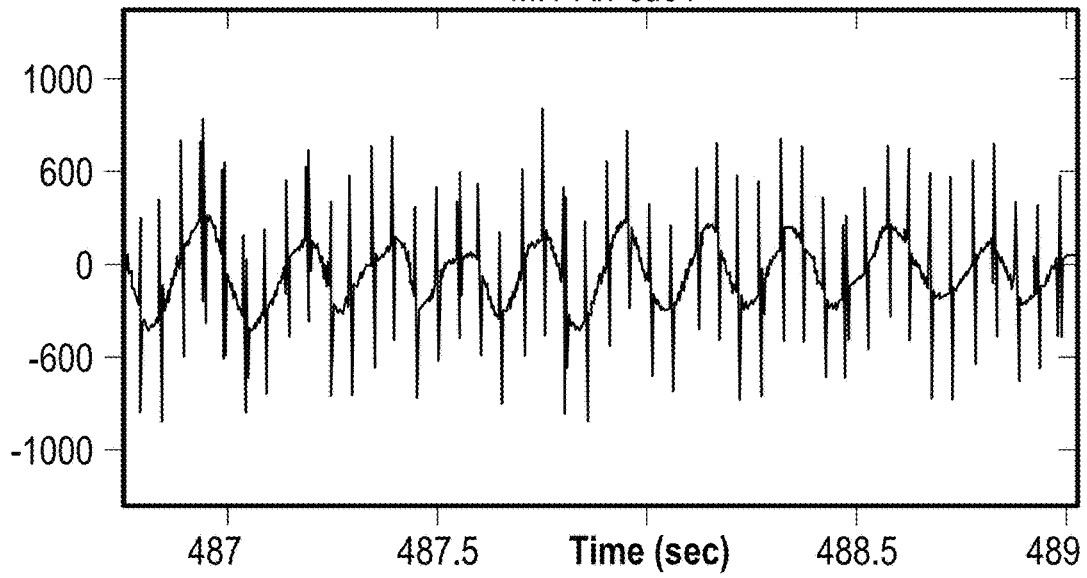
FIGS. 13A and 13B illustrate an ECG waveform indicative of ventricular fibrillation during application of neurostimulation without denoising and with denoising, respectively.
Figure 13B:
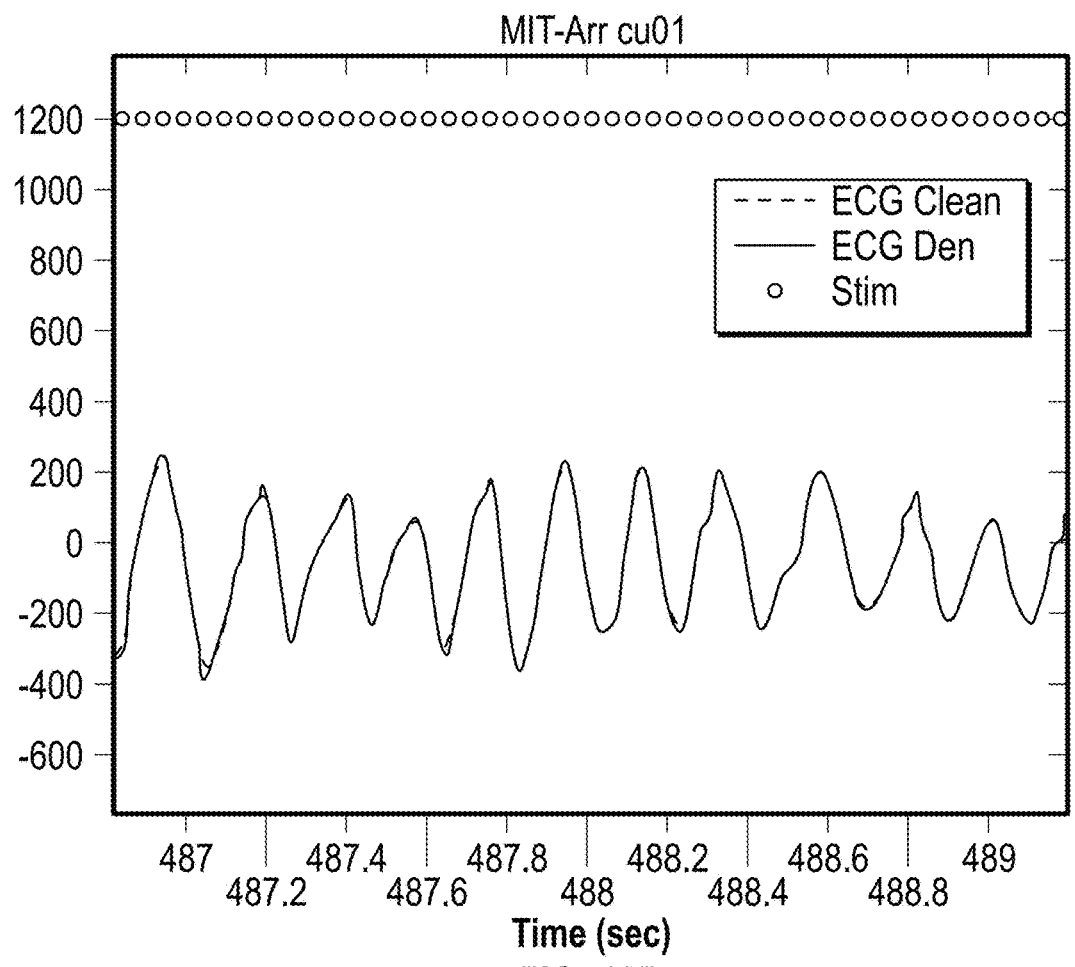

FIGS. 12A and 12B illustrate an ECG waveform indicative of atrial fibrillation during application of neurostimulation without denoising and with denoising, respectively. Again, the line $S_{peak}$ in FIG. 12B indicates the location of the original stimulation artifact, or transitory noise, spikes from FIG. 12A prior to denoising. FIGS. 13A and 13B illustrate an ECG waveform indicative of ventricular fibrillation during application of neurostimulation without denoising and with denoising, respectively.

The denoising processes and systems described herein may also be used to denoise ECG signals or other bio-signals or physiological signals (e.g., other cardiac-related signals correlated to a cardiac cycle, biophysical signals, blood pressure signals, respiratory rate signals, or any other electrical or electrochemical signal) when electromagnetic energy or pulses (e.g., electrical stimulation pulses) are applied to tissue other than nerves surrounding the pulmonary artery. For example, the denoising processes and systems described herein may also be used to denoise signals when other forms of tissue modulation or electrical energy application or other therapy is occurring or being performed (e.g., spinal neuromodulation, pacing with a pacemaker, defibrillation with an implantable defibrillator or external defibrillation system, pulsed electrocautery, stimulation of nerves to treat urinary or fecal incontinence, muscle stimulation, prostate stimulation, brain stimulation, stimulation of the vagus nerve, stimulation of osteoblasts, joint stimulation therapy to treat orthopedic conditions, iontophoresis, radiofrequency tissue ablation, etc.). In various implementations, the denoising processes and systems described herein may be used to denoise multiple waveforms or signals obtained from multiple different sources.

Figure 14:
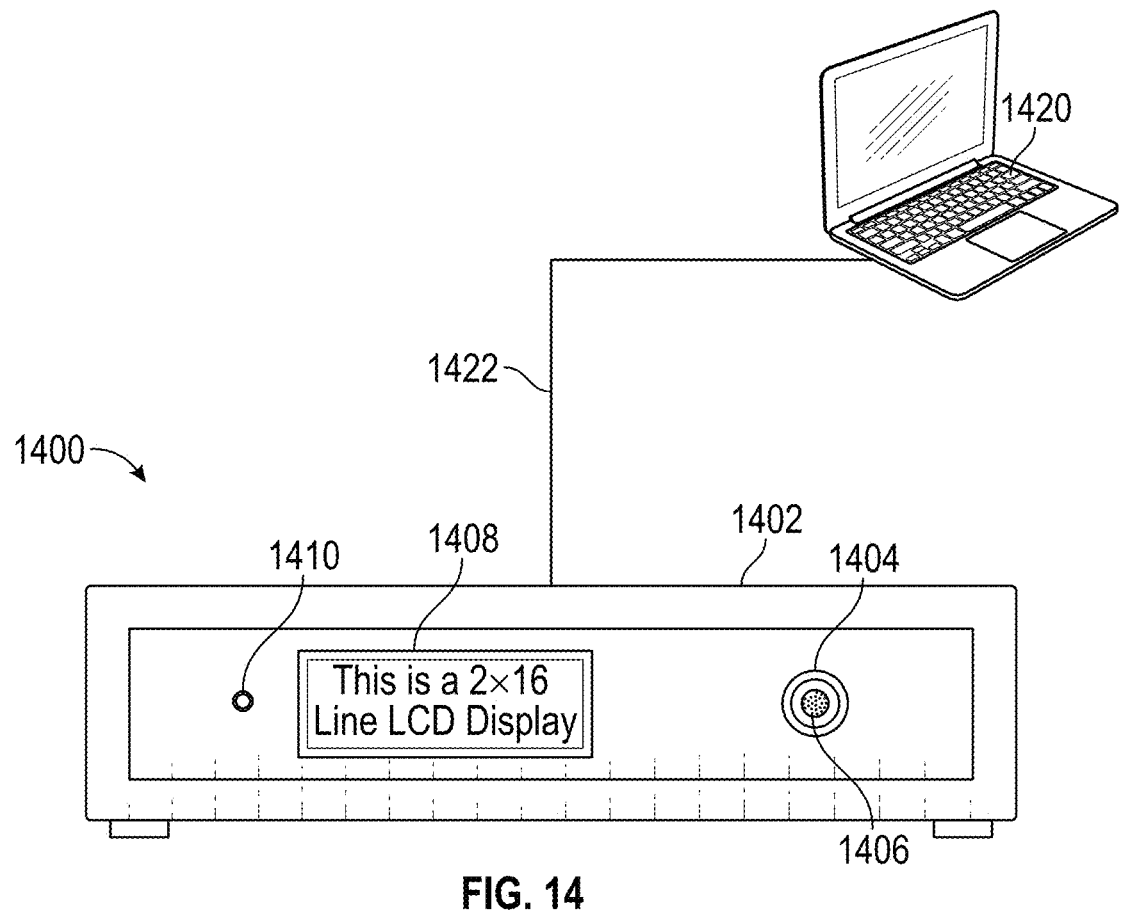
FIG. 14 is a front view of an example tissue modulation system (e.g., neurostimulation system).

FIG. 14 is a front view of an example stimulation system 1400 (e.g., neuromodulation system 410). The stimulation system 1400 comprises a housing 1402, a catheter connector 1404 including electrical connectors 1406, a display 1408, and an input button 1410 to allow a user to provide input with respect to the display 1408. The housing 1402 can contain stimulation electronics including a switch matrix for electrode stimulation. In some examples, a minimum output of the stimulation matrix is 25 mA, up to 8 ms, and 100 Hz. Other minimums, maximums, and specified parameters (e.g., number of polarities, pulsing mode, amplitude, phase, voltage, duration, inter-pulse interval, duty cycle, dwell time, sequence, waveform, etc.) are also possible. A computing device 1420 (e.g., networked computer terminal, desktop, laptop, tablet, smartphone, smartwatch, etc.) may be communicatively coupled to the stimulation system 1400 via wired or wireless system. The computing device 1420 may be the controller or control unit 412 in the schematic of FIG. 4. In some examples, a tablet may be connected to the stimulation system 1400 via a USB connection 1422 (e.g., as shown in FIG. 14). The computing device 1420 may include a display (e.g., touchscreen display) providing a graphical user interface configured to set stimulation parameters, present sensor data, view waveforms, store data, etc. The computing device 1420 may be networked to other computing devices, networks, the internet (e.g., via secured, HIPAA-compliant protocol), etc. The stimulation system may also include electrical connectors (not shown) that may be configured to interface with electrical connectors from ECG leads (e.g., three or more leads from skin ECG patches). The stimulation system 1400 may include additional electrical connectors that are not used to connect to current catheters, but that can provide the ability to update the system for future developments. The stimulation system 1400, the computing device 1420, and/or another computing device may include embedded programs for stimulation and/or sensing. The stimulation system 1400, the computing device 1420, and/or another computing device may include safety alarms configured to alert a user at the stimulation system 1400, the computing device 1420, and/or another computing device of an alarm event, such as those described herein.

In some implementations, the system comprises various features that are present as single features (as opposed to multiple features). For example, in one implementation, the system includes a single ECG device, a single denoising subsystem and a single neuromodulation subsystem. A single pressure sensor may also be included. The system may comprise a single patient monitor or display as described herein. Multiple features or components are provided in alternate implementations.

In some implementations, the system comprises one or more of the following: means for tissue modulation (e.g., an electrical stimulation system including a stimulation pulse generator, a catheter with one or more electrodes and/or sensors), means for removing stimulation artifact from biological or physiological parameter signals or waveforms (e.g., denoising system including one or more of an ADC, a DAC, amplifiers, multi-domain signal processing subsystems that comprise multiple different filters implemented in hardware and/or software), etc.

The foregoing description and examples has been set forth merely to illustrate the disclosure and are not intended as being limiting. Each of the disclosed aspects and examples of the present disclosure may be considered individually or in combination with other aspects, examples, and variations of the disclosure. In addition, unless otherwise specified, none of the steps of the methods of the present disclosure are confined to any particular order of performance. Modifications of the disclosed examples incorporating the spirit and substance of the disclosure may occur to persons skilled in the art and such modifications are within the scope of the present disclosure.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various examples described and the appended claims. Further, the disclosure herein of any particular feature, aspect, method, property, characteristic, quality, attribute, element, or the like in connection with an example can be used in all other examples set forth herein. Any methods disclosed herein need not be performed in the order recited. Depending on the example, one or more acts, events, or functions of any of the algorithms, methods, or processes described herein can be performed in a different sequence, can be added, merged, or left out altogether (e.g., not all described acts or events are necessary for the practice of the algorithm). In some examples, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each example. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some examples may be performed using the sequence of operations described herein, while other examples may be performed following a different sequence of operations.

The various illustrative logical blocks, modules, processes, methods, and algorithms described in connection with the examples disclosed herein can be implemented as electronic hardware, computer software, or combinations of both. To clearly illustrate this interchangeability of hardware and software, various illustrative components, blocks, modules, operations, and steps have been described above generally in terms of their functionality. In some implementations, the modules are modules for processing data, wherein the module is stored in a memory. The module may comprise software in the form of an algorithm or machine-readable instructions. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the examples disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The blocks, operations, or steps of a method, process, or algorithm described in connection with the examples disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular example.

The methods disclosed herein may include certain actions taken by a practitioner; however, the methods can also include any third-party instruction of those actions, either expressly or by implication. For example, actions such as "positioning an electrode" include "instructing positioning of an electrode."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 V" should include "1 V." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A, B, C, A and B, A and C, B and C, or A, B, and C.

What is claimed is:

1. A system comprising:
an electrical stimulation system; and
a denoising system comprising circuitry configured to:
receive original ECG signals from an ECG electrode array;
receive a synchronization signal from the electrical stimulation system indicative of initiation of electrical stimulation being applied by the electrical stimulation system;
denoise the original ECG signals after receipt of the synchronization signal via one or more denoising stages, wherein denoising the original ECG signals comprises blanking portions of the original ECG signals and modifying the blanked portions to provide modified ECG signals with reduced transitory noise;
determine that electrical stimulation has been stopped based on the synchronization signal; and
cause the original ECG signals to bypass the one or more denoising stages upon determining that electrical stimulation has stopped.

2. The system of claim 1, wherein the circuitry comprises one or more processors further configured to digitize the portions of the original ECG signals.

3. The system of claim 2, wherein the one or more processors are further configured to refine the modified ECG signals using at least one of a linear phase filter or a digital finite impulse response filter to create denoised ECG signals.

4. The system of claim 3, wherein the one or more processors are further configured to:
convert the denoised ECG signals into an analog signal to facilitate output on a display; and
output the denoised ECG signals for presentation on the display.

5. The system of claim 4, further comprising
a patient monitor comprising a display configured to display the output.

6. The system of claim 1, wherein said blanking comprises temporarily removing values stored at memory locations corresponding to the portions of the original ECG signals and wherein said modifying the blanked portions comprises interpolation, and wherein said interpolation comprises identifying a last value prior to said blanking and a first value after said blanking and replacing the removed values in the memory locations with interpolated values between the last value and the first value in the memory locations.

7. The system of claim 6, wherein the circuitry comprises one or more processors further configured to filter out 50 Hz or 60 Hz line frequency components for a time period prior to said blanking and following said blanking to ensure the first value and the last value are not affected by the 50 Hz or 60 Hz line frequency components.

8. The system of claim 1, wherein said blanking comprises temporarily removing values stored at memory locations corresponding to the portions of the original ECG signals and wherein said modifying the blanked portions comprises interpolation, and wherein said interpolation comprises calculating modified values to replace the removed values in the memory locations.

9. The system of claim 1, wherein said blanking comprises temporarily removing values stored at memory locations corresponding to the portions of the original ECG signals and wherein said modifying the blanked portions comprises replacing the removed values with a last known good value prior to said blanking.

10. The system of claim 1, wherein the circuitry comprises sample and hold circuitry.

11. The system of claim 1, wherein the electrical stimulation system is a cardio pulmonary nerve stimulation system.

12. The system of claim 1, further comprising one or more switches configured to open and close based on the synchronization signal.

13. The system of claim 1, wherein the synchronization signal is continuously delivered for a duration of the electrical stimulation.

14. A system comprising:
an electrical stimulation system; and
a denoising system comprising one or more processors configured to, upon execution of stored instructions on a non-transitory computer-readable medium:
receive one or more original ECG signals from an ECG electrode array;
receive a synchronization signal from the electrical stimulation system indicative of initiation of electrical stimulation being applied by the electrical stimulation system;
denoise the one or more original ECG signals after receipt of the synchronization signal via a denoising sub-process, wherein denoising the one or more original ECG signals comprises blanking portions of the one or more original ECG signals and modifying the blanked portions to provide one or more modified ECG signals with reduced transitory noise;
output the one or more modified ECG signals for display;
determine that electrical stimulation has been stopped based on the synchronization signal; and
cause the one or more original ECG signals to bypass the denoising sub-process upon determining that electrical stimulation has stopped.

15. The system of claim 14, further comprising an alert generation subsystem configured to generate an alert if a characteristic of the one or more original ECG signals is out of a threshold range.

16. The system of claim 15, wherein the characteristic is an R-R interval between successive R waves of the one or more original ECG signals.

17. The system of claim 14, wherein the electrical stimulation system is a cardio pulmonary nerve stimulation system.

18. The system of claim 14, further comprising one or more switches configured to open and close based on the synchronization signal.

19. The system of claim 14, wherein the synchronization signal is continuously delivered for a duration of the electrical stimulation.

20. The system of claim 19, wherein the synchronization signal is in an "on" state when electrical stimulation is being applied and in an "off" state when electrical stimulation has stopped.

* * * * *